US010562940B2

(12) United States Patent
Ross et al.

(10) Patent No.: US 10,562,940 B2
(45) Date of Patent: Feb. 18, 2020

(54) COMPUTATIONALLY OPTIMIZED BROADLY REACTIVE ANTIGENS FOR H1N1 INFLUENZA

(71) Applicant: University of Pittsburgh—Of the Commonwealth System of Higher Education, Pittsburgh, PA (US)

(72) Inventors: Ted M. Ross, Athens, GA (US); Corey J. Crevar, North Huntingdon, PA (US)

(73) Assignee: University of Pittsburgh— Of the Commonwealth System of Higher Education, Pittsburgh, PA (US)

(*) Notice: Subject to any disclaimer, the term of this patent is extended or adjusted under 35 U.S.C. 154(b) by 0 days.

(21) Appl. No.: 16/119,501

(22) Filed: Aug. 31, 2018

(65) Prior Publication Data

US 2018/0371025 A1 Dec. 27, 2018

Related U.S. Application Data

(62) Division of application No. 15/407,502, filed on Jan. 17, 2017, now Pat. No. 10,093,703, which is a division of application No. 14/126,550, filed as application No. PCT/US2012/043347 on Jun. 20, 2012, now Pat. No. 9,580,475.

(60) Provisional application No. 61/498,800, filed on Jun. 20, 2011.

(51) Int. Cl.

| *C07K 14/005* | (2006.01) |
| *A61K 39/12* | (2006.01) |
| *A61K 39/145* | (2006.01) |
| *C12N 7/00* | (2006.01) |
| *A61K 39/00* | (2006.01) |

(52) U.S. Cl.
CPC ............ *C07K 14/005* (2013.01); *A61K 39/12* (2013.01); *A61K 39/145* (2013.01); *C12N 7/00* (2013.01); *A61K 2039/5258* (2013.01); *A61K 2039/55505* (2013.01); *C12N 2760/16122* (2013.01); *C12N 2760/16123* (2013.01); *C12N 2760/16134* (2013.01)

(58) Field of Classification Search
None
See application file for complete search history.

(56) References Cited

U.S. PATENT DOCUMENTS

| 7,566,454 | B2 | 7/2009 | Lu et al. | |
| 9,309,290 | B2* | 4/2016 | Ross | C07K 14/005 |
| 9,580,475 | B2* | 2/2017 | Ross | A61K 39/12 |
| 10,093,703 | B2* | 10/2018 | Ross | A61K 39/12 |
| 2005/0181459 | A1 | 8/2005 | Baker et al. | |
| 2008/0003239 | A1* | 1/2008 | Duke | A61K 39/145 |
| | | | | 424/206.1 |
| 2008/0045472 | A1 | 2/2008 | Brahmachari et al. | |
| 2009/0074803 | A1 | 3/2009 | Sallberg et al. | |
| 2009/0291472 | A1 | 11/2009 | Lu et al. | |
| 2009/0327170 | A1 | 12/2009 | Donati et al. | |
| 2010/0041740 | A1 | 2/2010 | Wong et al. | |
| 2010/0166769 | A1* | 7/2010 | Hsiao | A61K 39/145 |
| | | | | 424/159.1 |
| 2018/0371025 | A1* | 12/2018 | Ross | A61K 39/12 |

FOREIGN PATENT DOCUMENTS

| JP | 2004-501647 | 1/2004 |
| JP | 2007-529997 | 11/2007 |
| JP | 2009-502789 | 1/2009 |
| WO | WO 2002/000885 | 1/2002 |
| WO | WO 2005/020889 | 3/2005 |
| WO | WO 2007/011904 | 1/2007 |
| WO | WO 2008/028946 | 3/2008 |
| WO | WO 2009/073330 | 6/2009 |
| WO | WO 2010/003225 | 1/2010 |
| WO | WO 2010/036948 | 4/2010 |
| WO | WO 2010/036970 | 4/2010 |
| WO | WO 2010/115133 | 10/2010 |
| WO | WO 2011/094358 | 8/2011 |
| WO | WO 2012/036993 | 3/2012 |
| WO | WO 2013/119683 | 8/2013 |
| WO | WO 2013/122827 | 8/2013 |
| WO | WO 2013/148164 | 10/2013 |

OTHER PUBLICATIONS

Cai et al., "A Computational Framework for Influenza Antigenic Cartography," *PLoS Comput. Biol.*, vol. 6:e1000949, 2010.
Carter et al., "Complex Patterns of Human Antisera Reactivity to Novel 2009 H1N1 and Historical H1N1 Influenza Strains," *PLoS ONE* 7(7):e39435, 2012.
Chen et al., "A consensus-hemagglutinin-based DNA vaccine that protects mice against divergent H5N1 influenza viruses," *Proc Natl Acad Sci USA* 105(36):16538-13543, 2008.
Ekiert et al., "Antibody recognition of a highly conserved influenza virus prevention and therapy," *Science* 324(5924):246-251, 2009.
Fenimore et al., "Designing and Testing Broadly-Protective Filoviral Vaccines Optimized for Cytotoxic T-Lymphocyte Epitope Coverage," *PLoS ONE* 7(10):e44769, 2012.
GenBank Accession No. ABA55715, Oct. 8, 2005.
GenBank Accession No. ABD60856.1, Mar. 2, 2006.

(Continued)

*Primary Examiner* — Shanon A. Foley
(74) *Attorney, Agent, or Firm* — Klarquist Sparkman, LLP

(57) ABSTRACT

Described herein is the generation of optimized H1N1 influenza HA polypeptides for eliciting a broadly reactive immune response to H1N1 influenza virus isolates. The optimized HA polypeptides were developed through a series of HA protein alignments, and subsequent generation of consensus sequences, based on selected H1N1 viruses isolated from 1918-2011. Provided herein are optimized H1N1 HA polypeptides, and compositions, fusion proteins and VLPs comprising the HA polypeptides. Further provided are codon-optimized nucleic acid sequences encoding the HA polypeptides. Methods of eliciting an immune response against influenza virus in a subject are also provided by the present disclosure.

18 Claims, 7 Drawing Sheets

Specification includes a Sequence Listing.

(56) References Cited

OTHER PUBLICATIONS

GenBank Accession No. AB044123, Mar. 22, 2007.
GenBank Accession No. ABQ44416, May 16, 2007.
GenBank Accession No. ABF47748, May 8, 2006.
GenBank Accession No. ABU99095, May 1, 2008.
GenBank Accession No. ABW21677, Mar. 12, 2010.
GenBank Accession No. EU195416, Mar. 12, 2010.
Giles et al., "A Computationally Optimized Hemagglutinin Virus-Like Particle Elicits Broadly Reactive Antibodies that Protect Nonhuman Primates from H5N1 Infection," *J Infect Dis* 205(10):1562-1570, 2012.
Giles et al., "A Computationally Optimized Broadly Reactive Antigen (COBRA) Based H5N1 VLP Vaccine Elicits Broadly Reactive Antibodies in Mice and Ferrets," *Vaccine*, vol. 29:3043-3054, 2011.
Giles et al., "Computationally Optimized Antigens to Overcome Influenza Viral Diversity," *Expert Review of Vaccines*, vol. 11:267-269, 2012.
Giles et al., "Antibody Breadth and Protective Efficacy are Increased by Vaccination with Computationally Optimized Hemagglutinin but not with Polyvalent Hemagglutinin-Based H5N1 Virus-Like Particle Vaccines," *Clin. Vaccine Immunol.*, vol. 19:128-139, 2012.
Jiang et al., "Enhanced Protective Efficacy of H5 Subtype Avian Influenza DNA Vaccine with Codon Optimized HA Gene in a pCAGGS Plasmid Vector," *Antiviral Res.*, vol. 75:234-241, 2007.
Laddy et al., "Immunogenicity of novel consensus-based DNA vaccines against avian influenza," *Vaccine* 25:2984-2989, 2007.
Parida et al., "Computational Analysis of Proteome of H5N1 Avian Influenza Virus to Define T Cell Epitopes with Vaccine Potential," *Vaccine*, vol. 25:7530-7539, 2007.
Prabakaran et al., "Neutralizing Epitopes of Influenza Virus Hemagglutinin: Target for the Development of a Universal Vaccine against H5N1 Lineages," *J Virol* 84(22):11822-11830, 2010.
Pushko et al., "Recombinant H1N1 Virus-Like Particle Vaccine Elicits Protective Immunity in Ferrets Against the 2009 Pandemic H1N1 Influenza Virus," *Vaccine*, vol. 28:4771-4776, 2010.
Somvanshi et al., "Prediction of Epitopes in Hemagglutinin and Neuraminidase Proteins of Influenza A Virus H5N1 Strain: A Clue for Diagnostic and Vaccine Development," *OMICS* vol. 12:61-69, 2008.
Tang et al., "Hemagglutinin Displayed Baculovirus Protects Against Highly Pathogenic Influenza," *Vaccine*, vol. 28:6821-6831, 2010.
Tang et al., Characterization of Duck H5N1 Influenza Viruses with Differing Pathogenicity in Mallard (*Anas platyrhynchos*) Ducks, *Avian Pathol.*, vol. 38:457-467, 2009.
Tao et al., "Virus-Like Particle Vaccine Comprised of the HA, NA, and M1 Proteins of an Avian Isolated H5N1 Influenza Virus Induces Protective Immunity Against Homologous and Heterologous Strains in Mice," *Viral Immunol.*, vol. 22:273-281, 2009.
Tenbusch et al., "Condon-Optimization of the Hemagglutinin Gene from the Novel Swine Origin H1N1 Influenza Virus has Differential Effects on $CD4^+$ T-Cell Responses and Immune Effector Mechanisms following DNA Electroporation in Mice," *Vaccine*, vol. 28:3273-3277, 2010.
UniProt Accession No. A4U6Y5, May 15, 2007.
Uniprot Accession No. A4JZ83, version 33, deposited May 3, 2011 (2 pages).
Uniprot Accession No. A5GX63, version 32, deposited May 3, 2011 (2 pages).
Uniprot Accession No. B7NZ42, version 20, deposited May 3, 2011 (2 pages).
Uniprot Accession No. B6A6V2, Apr. 2006.
Uniprot Accession No. Q289C8, May 2007.
Uniprot Accession No. Q1I1V4, Jun. 2006.
Uniprot Accession No. QOP3B4, Sep. 2006.
Wang et al., "Hemagglutinin (HA) Proteins from H1 and H3 Serotypes of Influenza A Viruses Require Different Antigen Designs for the Induction of Optimal Protective Antibody Responses as Studied by Codon-Optimized HA DNA Vaccines," *J. Virol.*, vol. 80:11628-11637, 2006.
Weaver et al., "Protection against Divergent Influenza H1N1 Virus by a Centralized Influenza Hemagglutinin," *PLoS ONE* 6(3):e18314, Mar. 28, 2011.
Zhao et al., "Induction of protection of against divergent H5N1 influenza viruses using a recombinant fusion protein linking influenza M2e to *Onchocerca volvulus* activation associated protein-1 (ASP-1) adjuvant," *Vaccine*, vol. 28:7233-7240, 2010.

* cited by examiner

COMPUTATIONALLY OPTIMIZED BROADLY REACTIVE ANTIGENS FOR H1N1 INFLUENZA

CROSS REFERENCE TO RELATED APPLICATIONS

This is a divisional of U.S. application Ser. No. 15/407,502, filed Jan. 17, 2017, which is a divisional of U.S. application Ser. No. 14/126,550, filed Dec. 16, 2013, issued as U.S. Pat. No. 9,580,475 on Feb. 28, 2017, which is the U.S. National Stage of International Application No. PCT/US2012/043347, filed Jun. 20, 2012, published in English under PCT Article 21(2), which claims the benefit of U.S. Provisional Application No. 61/498,800, filed Jun. 20, 2011. The above-listed applications are herein incorporated by reference in their entirety.

FIELD

This disclosure concerns optimized influenza hemagglutinin proteins that elicit broadly reactive immune responses to H1N1 virus isolates and their use as vaccines.

BACKGROUND

Influenza virus is a member of Orthomyxoviridae family. There are three subtypes of influenza viruses, designated influenza A, influenza B, and influenza C. The influenza virion contains a segmented negative-sense RNA genome, which encodes the following proteins: hemagglutinin (HA), neuraminidase (NA), matrix (M1), proton ion-channel protein (M2), nucleoprotein (NP), polymerase basic protein 1 (PB1), polymerase basic protein 2 (PB2), polymerase acidic protein (PA), and nonstructural protein 2 (NS2). The HA, NA, M1, and M2 are membrane associated, whereas NP, PB1, PB2, PA, and NS2 are nucleocapsid associated proteins. The M1 protein is the most abundant protein in influenza particles. The HA and NA proteins are envelope glycoproteins, responsible for virus attachment and penetration of the viral particles into the cell, and the sources of the major immunodominant epitopes for virus neutralization and protective immunity. Both HA and NA proteins are considered the most important components for prophylactic influenza vaccines.

Each year, seasonal influenza causes over 300,000 hospitalizations and 36,000 deaths in the U.S. alone (Simonsen et al., *Lancet Infect Dis* 7:658-66, 2007). The emergence of the novel H1N1 influenza virus in 2009 demonstrated how quickly a new influenza pandemic can sweep across the world.

There are currently two influenza vaccine approaches licensed in the United States—the inactivated, split vaccine and the live-attenuated virus vaccine. The inactivated vaccines can efficiently induce humoral immune responses but generally only poor cellular immune responses. Live virus vaccines cannot be administered to immunocompromised or pregnant patients due to their increased risk of infection. Thus, a need exists for a broadly protective influenza virus vaccine.

SUMMARY

Disclosed herein is the generation of optimized H1N1 influenza HA polypeptides for eliciting a broadly reactive immune response to H1N1 influenza virus isolates. The optimized HA polypeptides were developed through a series of HA protein alignments, and subsequent generation of consensus sequences, based on selected H1N1 viruses isolated from 1918-2011.

Provided herein are recombinant influenza HA polypeptides having an optimized amino acid sequence for eliciting a broadly reactive immune response against H1N1 influenza. In some embodiments, the HA polypeptide comprises an amino acid sequence at least 95%, at least 96%, at least 97%, at least 98% or at least 99% identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11. In some embodiments, the amino acid sequence of the polypeptide comprises no more than 5, no more than 6, no more than 7, no more than 8, no more than 9 or no more than 10 amino acid substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11. In some embodiments, the influenza HA polypeptide lacks the N-terminal methionine residue.

Isolated nucleic acid molecules and vectors encoding the recombinant HA polypeptides are also provided by the present disclosure. Further provided are isolated cells comprising such vectors.

Also provided are influenza virus-like particles (VLPs) and fusion proteins comprising the optimized HA polypeptides disclosed herein.

Further provided are compositions that include the optimized influenza HA polypeptides, fusion proteins or VLPs disclosed herein in a pharmaceutically acceptable carrier. Methods of eliciting an immune response against influenza virus in a subject by administering the disclosed compositions, fusion proteins or VLPs is also provided by the present disclosure.

Also provided are methods of immunizing a subject against influenza virus by administering to the subject a composition comprising a VLP that contains an optimized HA polypeptide.

The foregoing and other objects, features, and advantages of the disclosure will become more apparent from the following detailed description, which proceeds with reference to the accompanying figures.

SEQUENCE LISTING

Figure 1:
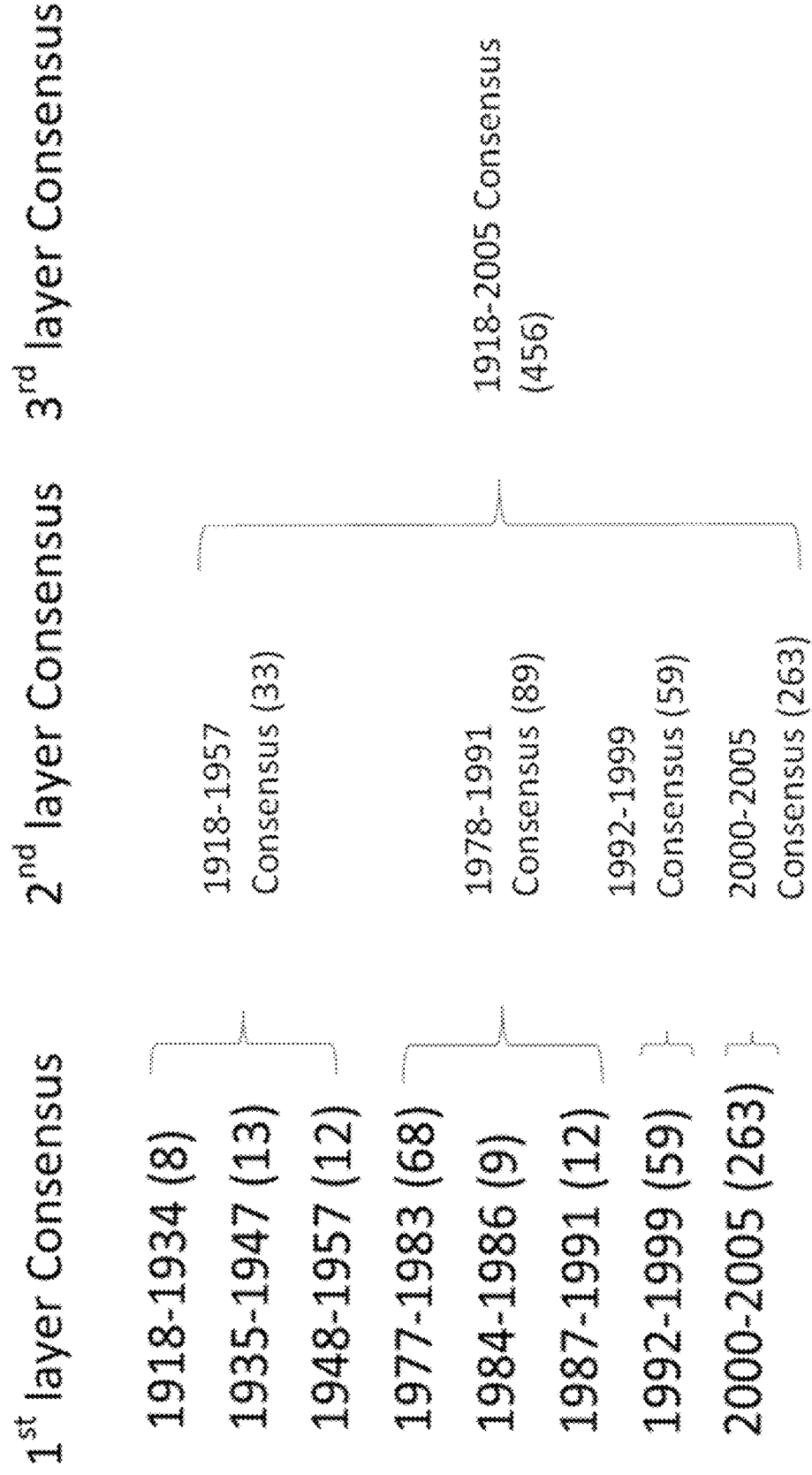
FIG. 1 is a schematic of the process used to generate an H1N1 HA consensus sequence according to Method 1.

The nucleic and amino acid sequences listed in the accompanying sequence listing are shown using standard letter abbreviations for nucleotide bases, and three letter code for amino acids, as defined in 37 C.F.R. 1.822. Only one stand of each nucleic acid sequence is shown, but the complementary strand is understood as included by any reference to the displayed strand. The Sequence Listing is submitted as an ASCII text file, created on Aug. 21, 2018, 67.7 KB, which is incorporated by reference herein. In the accompanying sequence listing:

SEQ ID NOs: 1-11 are the amino acid sequences of optimized H1N1 HA proteins.

SEQ ID NO: 12 is a consensus amino acid sequence of the optimized H1N1 HA proteins.

SEQ ID NO: 13 is the nucleic acid sequence of a codon-optimized H1N1 HA.

DETAILED DESCRIPTION

I. Abbreviations

COBRA: computationally optimized broadly reactive antigen

HA: hemagglutinin

HAI: hemagglutination inhibition

HRP: horseradish peroxidase

M1: matrix protein 1

NA: neuraminidase

PFU: plaque form unit

VLP: virus-like particle

II. Terms and Methods

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition to a subject means to give, apply or bring the composition into contact with the subject. Administration can be accomplished by any of a number of routes, such as, for example, topical, oral, subcutaneous, intramuscular, intraperitoneal, intravenous, intrathecal and intradermal.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In some embodiments of the disclosed compositions and methods, the antigen is an influenza HA protein.

Codon-optimized: A "codon-optimized" nucleic acid refers to a nucleic acid sequence that has been altered such that the codons are optimal for expression in a particular system (such as a particular species of group of species). For example, a nucleic acid sequence can be optimized for expression in mammalian cells. Codon optimization does not alter the amino acid sequence of the encoded protein.

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain to internal stop codons. For example, a fusion protein includes an influenza HA fused to a heterologous protein.

Hemagglutinin (HA): An influenza virus surface glycoprotein. HA mediates binding of the virus particle to a host cells and subsequent entry of the virus into the host cell. The nucleotide and amino acid sequences of numerous influenza HA proteins are known in the art and are publically available, such as those deposited with GenBank. HA (along with NA) is one of the two major influenza virus antigenic determinants.

Immune response: A response of a cell of the immune system, such as a B-cell, T-cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immunogen: A compound, composition, or substance which is capable, under appropriate conditions, of stimulating an immune response, such as the production of antibodies or a T-cell response in an animal, including compositions that are injected or absorbed into an animal. As used herein, an "immunogenic composition" is a composition comprising an immunogen (such as an HA polypeptide).

Immunize: To render a subject protected from an infectious disease, such as by vaccination.

Influenza virus: A segmented negative-strand RNA virus that belongs to the Orthomyxoviridae family. There are three types of Influenza viruses, A, B and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as H5N1, cause systemic infections in poultry in which mortality may reach 100%. In 2009, H1N1 influenza was the most common cause of human influenza. A new strain of swine-origin H1N1 emerged in 2009 and was declared pandemic by the World Health Organization. This strain was referred to as "swine flu." H1N1 influenza A viruses were also responsible for the Spanish flu pandemic in 1918, the Fort Dix outbreak in 1976, and the Russian flu epidemic in 1977-1978.

Isolated: An "isolated" biological component (such as a nucleic acid, protein or virus) has been substantially separated or purified away from other biological components (such as cell debris, or other proteins or nucleic acids). Biological components that have been "isolated" include those components purified by standard purification methods. The term also embraces recombinant nucleic acids, proteins or viruses (or VLPs), as well as chemically synthesized nucleic acids or peptides.

Linker: One or more amino acids that serve as a spacer between two polypeptides of a fusion protein.

Matrix (M1) protein: An influenza virus structural protein found within the viral envelope. M1 is thought to function in assembly and budding.

Neuraminidase (NA): An influenza virus membrane glycoprotein. NA is involved in the destruction of the cellular receptor for the viral HA by cleaving terminal sialic acid residues from carbohydrate moieties on the surfaces of infected cells. NA also cleaves sialic acid residues from viral proteins, preventing aggregation of viruses. NA (along with HA) is one of the two major influenza virus antigenic determinants.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Optimized influenza HA protein: As used herein, "optimized influenza HA protein" refers to the HA protein consensus sequence generated by sequence alignments of selected H1N influenza viruses isolated between 1918 and 2011 (as described in Example 1 below). The nucleotide sequences encoding optimized HA proteins were (or can be) further optimized for expression in mammalian cells via codon-optimization and RNA optimization (such as to increase RNA stability). Optimized influenza HA proteins disclosed herein (and set forth herein as SEQ ID NOs: 1-11) are also referred to as "COBRA" sequences. Optimized HA polypeptides are designed to elicit broadly reactive immune responses in a subject. In the context of the present disclosure, "broadly reactive" means the protein sequence elicits an immune response in a subject that is sufficient to inhibit, neutralize or prevent infection of a broad range of influenza viruses (such as most or all influenza viruses within a specific subtype). In some instances, the optimized influenza HA protein is capable of eliciting an immune response, such as a protective immune response, against most or all H1N1 influenza virus isolates.

Outbreak: As used herein, an influenza virus "outbreak" refers to a collection of virus isolates from within a single country in a given year.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compositions, such as one or more influenza vaccines, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |

| Original Residue | Conservative Substitutions |
| --- | --- |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In some embodiments herein, the promoter is a CMV promoter.

Purified: The term "purified" does not require absolute purity; rather, it is intended as a relative term. Thus, for example, a purified peptide, protein, virus, VLP or other active compound is one that is isolated in whole or in part from naturally associated proteins and other contaminants. In certain embodiments, the term "substantially purified" refers to a peptide, protein, virus, VLP or other active compound that has been isolated from a cell, cell culture medium, or other crude preparation and subjected to fractionation to remove various components of the initial preparation, such as proteins, cellular debris, and other components.

Recombinant: A recombinant nucleic acid, protein, virus or VLP is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.* 6:119-129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Subject: Living multi-cellular vertebrate organisms, a category that includes both human and non-human mammals, such as non-human primates.

Therapeutically effective amount: A quantity of a specified agent sufficient to achieve a desired effect in a subject being treated with that agent. For example, this may be the amount of an influenza virus vaccine useful for eliciting an immune response in a subject and/or for preventing infection or disease caused by influenza virus. Ideally, in the context of the present disclosure, a therapeutically effective amount of an influenza vaccine is an amount sufficient to increase resistance to, prevent, ameliorate, and/or treat infection caused by influenza virus in a subject without causing a substantial cytotoxic effect in the subject. The effective amount of an influenza vaccine useful for increasing resistance to, preventing, ameliorating, and/or treating infection in a subject will be dependent on, for example, the subject being treated, the manner of administration of the therapeutic composition and other factors.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vaccine: A preparation of immunogenic material capable of stimulating an immune response, administered for the prevention, amelioration, or treatment of disease, such as an infectious disease. The immunogenic material may include, for example, attenuated or killed microorganisms (such as attenuated viruses), or antigenic proteins, peptides or DNA derived from them. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of an inserted gene or genes. In some embodiments of the present disclosure, the vector encodes an influenza HA, NA or M1 protein. In some embodiments, the vector is the pTR600 expression vector (U.S. Patent Application Publication No. 2002/0106798; Ross et al., *Nat Immunol.* 1(2):102-103, 2000; Green et al., *Vaccine* 20:242-248, 2001).

Virus-like particle (VLP): Virus particles made up of one of more viral structural proteins, but lacking the viral genome. Because VLPs lack a viral genome, they are non-infectious. In addition, VLPs can often be produced by heterologous expression and can be easily purified. Most VLPs comprise at least a viral core protein that drives budding and release of particles from a host cell. One example of such a core protein is influenza M1. In some embodiments herein, an influenza VLP comprises the HA, NA and/or M1 proteins. Influenza VLPs can be produced by transfection of host cells with plasmids encoding the HA and NA proteins, and optionally the M1 protein. After incubation of the transfected cells for an appropriate time to allow for protein expression (such as for approximately 72 hours), VLPs can be isolated from cell culture supernatants. Example 2 provides an exemplary protocol for purifying influenza VLPs from cell supernatants. In this example, VLPs are isolated by low speed centrifugation (to remove cell debris), vacuum filtration and ultracentrifugation through 20% glycerol. Other methods of producing influenza VLPs are known in the art (see, for example, U.S. Patent Application Publication Nos. 2006/0263804; 2008/0031895; 2010/0166769; and 2010/0239610).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

II. Overview of Several Embodiments

Disclosed herein is the generation of optimized H1N1 influenza HA polypeptides for eliciting a broadly reactive immune response to H1N1 influenza. The optimized HA polypeptides were developed through a series of HA protein alignments, and subsequent generation of consensus sequences, based on selected H1N1 viruses isolated from 1918-2011. The methods used to generate the 11 HA consensus sequences are described in Example 1 and FIGS. 1-5. The amino acid sequences of the 11 consensus HA polypeptides are set forth herein as SEQ ID NOs: 1-11. In addition, an amino acid consensus sequence of SEQ ID NOs: 1-11 is provided herein as SEQ ID NO: 12.

Provided herein are recombinant influenza HA polypeptides having an optimized amino acid sequence for eliciting a broadly reactive immune response against H1N1 influenza. In some embodiments, the HA polypeptide comprises an amino acid sequence at least 95%, at least 96%, at least 97%, at least 98% or at least 99% identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11. In other embodiments, the amino acid sequence of the polypeptide comprises no more than 5, no more than 6, no more than 7, no more than 8, no more than 9 or no more than 10 amino acid substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11.

In particular embodiments, provided is a recombinant influenza HA polypeptide comprising an amino acid sequence at least 99% identical to SEQ ID NO: 1; at least 99.2% identical to SEQ ID NO: 2; at least 99% identical to SEQ ID NO: 3; at least 99% identical to SEQ ID NO: 4; at least 98% or at least 99% identical to SEQ ID NO: 5; at least 99% identical to SEQ ID NO: 6; at least 97%, at least 98% or at least 99% identical to SEQ ID NO: 7; at least 99% identical to SEQ ID NO: 8; comprising SEQ ID NO: 9; at least 99% identical to SEQ ID NO: 10; or at least 99% identical to SEQ ID NO: 11.

In other particular embodiments, the recombinant influenza HA polypeptide comprises an amino acid sequence at least 99% identical to residues 2-566 of SEQ ID NO: 1; at least 99.2% identical to residues 2-566 of SEQ ID NO: 2; at least 99% identical to residues 2-566 of SEQ ID NO: 3; at least 99% identical to residues 2-566 of SEQ ID NO: 4; at least 98% or at least 99% identical to residues 2-566 of SEQ ID NO: 5; at least 99% identical to residues 2-566 of SEQ ID NO: 6; at least 97%, at least 98% or at least 99% identical to residues 2-566 of SEQ ID NO: 7; at least 99% identical to residues 2-566 of SEQ ID NO: 8; comprising residues 2-566 of SEQ ID NO: 9; at least 99% identical to residues 2-566 of SEQ ID NO: 10; or at least 99% identical to residues 2-566 of SEQ ID NO: 11.

In other embodiments, the amino acid sequence of the HA polypeptide comprises (i) no more than 5, nor more than 4, no more than 3, no more than 2 or no more than 1 amino acid substitution(s) relative to SEQ ID NO: 1; (ii) no more than 4, no more than 3, no more than 2 or no more than 1 amino acid substitution(s) relative to SEQ ID NO: 2; (iii) no more than 6, no more than 5, nor more than 4, no more than 3, no more than 2 or no more than 1 amino acid substitution(s) relative to SEQ ID NO: 3; (iv) no more than 8, no more than 7, no more than 6, no more than 5, nor more than 4, no more than 3, no more than 2 or no more than 1 amino acid substitution(s) relative to SEQ ID NO: 4; (v) no more than 10, no more than 9, no more than 8, no more than 7, no more than 6, no more than 5, nor more than 4, no more than 3, no more than 2 or no more than 1 amino acid substitution(s) relative to SEQ ID NO: 5; (vi) no more than 8, no more than 7, no more than 6, no more than 5, nor more than 4, no more than 3, no more than 2 or no more than 1 amino acid substitution(s) relative to SEQ ID NO: 6; (vii) no more than 10, no more than 9, no more than 8, no more than 7, no more than 6, no more than 5, nor more than 4, no more than 3, no more than 2 or no more than 1 amino acid substitution(s) relative to SEQ ID NO: 7; (viii) no more than 10, no more than 9, no more than 8, no more than 7, no more than 6, no more than 5, nor more than 4, no more than 3, no more than 2 or no more than 1 amino acid substitution(s) relative to SEQ ID NO: 8; (ix) no more than 8, no more than 7, no more than 6, no more than 5, nor more than 4, no more than 3, no more than 2 or no more than 1 amino acid substitution(s) relative to SEQ ID NO: 10; or (x) no more than 5, nor more than 4, no more than 3, no more than 2 or no more than 1 amino acid substitution(s) relative to SEQ ID NO: 11.

In some examples, the influenza HA polypeptide comprises or consists of the amino acid sequence of residues 2-566 of SEQ ID NO: 1, residues 2-566 of SEQ ID NO: 2, residues 2-566 of SEQ ID NO: 3, residues 2-566 of SEQ ID NO: 4, residues 2-566 of SEQ ID NO: 5, residues 2-566 of SEQ ID NO: 6, residues 2-566 of SEQ ID NO: 7, residues 2-566 of SEQ ID NO: 8, residues 2-566 of SEQ ID NO: 9, residues 2-566 of SEQ ID NO: 10 or residues 2-566 of SEQ ID NO: 11.

In other examples, the recombinant HA polypeptide comprises or consists of the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11.

In another example, the recombinant HA polypeptide comprises or consists of the amino acid sequence of SEQ ID NO: 12. In yet another example, the recombinant HA polypeptide comprises or consists of the amino acid sequence of residues 2-566 of SEQ ID NO: 12.

Further provided are isolated nucleic acid molecules encoding the recombinant HA polypeptides disclosed herein. In some embodiments, the nucleic acid molecule is codon-optimized for expression in mammalian cells. The nucleic acid molecule is optionally further optimized for RNA stability. In some embodiments, the sequence of the nucleic acid molecule is at least 95%, at least 96%, at least 97%, at least 98% or at least 99% identical to SEQ ID NO: 13. In particular examples, the sequence of the nucleic acid molecule comprises or consists of SEQ ID NO: 13.

Vectors comprising the nucleic acid molecules encoding recombinant HA polypeptides are also provided by the present disclosure. The vector can be any suitable vector for expression of the HA polypeptide, such as a mammalian expression vector. In particular examples, the vector is the pTR600 expression vector (U.S. Patent Application Publication No. 2002/0106798, herein incorporated by reference; Ross et al., *Nat Immunol.* 1(2):102-103, 2000; Green et al., *Vaccine* 20:242-248, 2001).

In some examples, the vector includes a promoter operably linked to the nucleic acid sequence encoding the HA polypeptide. In particular examples, the promoter is a CMV promoter.

Also provided are isolated cells comprising the disclosed vectors. In some cases, the cell is any suitable cell type for production and expression of VLPs, such as a mammalian cell.

Further provided are influenza VLPs comprising an optimized HA polypeptide disclosed herein. The influenza VLPs can further include any additional influenza proteins necessary to form the virus particle. In some embodiments, the influenza VLPs further include influenza neuraminidase (NA) protein, influenza matrix (M1) protein, or both.

Also provided are influenza VLPs comprising an influenza HA polypeptide disclosed herein, produced by transfecting a host cell with a vector encoding the HA polypeptide, a vector encoding an influenza NA protein and a vector encoding an influenza M1 protein under conditions sufficient to allow for expression of the HA, M1 and NA proteins.

Fusion proteins comprising an optimized influenza HA polypeptide are further provided by the present disclosure.

Also provided herein are compositions comprising an optimized influenza HA protein as disclosed herein, or a fusion protein or VLP comprising the optimized influenza HA protein. In some embodiments, the compositions further comprise a pharmaceutically acceptable carrier and/or an adjuvant. For example, the adjuvant can be alum, Freund's complete adjuvant, a biological adjuvant or immunostimulatory oligonucleotides (such as CpG oligonucleotides).

Further provided is a method of eliciting an immune response to influenza virus in a subject by administering an optimized influenza HA protein, fusion proteins containing an optimized influenza HA, VLPs containing an optimized influenza HA, or compositions thereof, as disclosed herein. In some embodiments, the influenza virus is an H1N1 influenza virus. In some embodiments, the HA protein, HA fusion protein or VLP can be administered using any suitable route of administration, such as, for example, intramuscular. In some embodiments, the HA protein, fusion protein or VLP is administered as a composition further comprising a pharmaceutically acceptable carrier and/or an adjuvant. For example, the adjuvant can be alum, Freund's complete adjuvant, a biological adjuvant or immunostimulatory oligonucleotides (such as CpG oligonucleotides).

Also provided is a method of immunizing a subject against influenza virus by administering to the subject VLPs containing an optimized influenza HA protein disclosed herein, or administering a composition thereof. In some embodiments of the method, the composition further comprises a pharmaceutically acceptable carrier and/or an adjuvant. For example, the adjuvant can be alum, Freund's complete adjuvant, a biological adjuvant or immunostimulatory oligonucleotides (such as CpG oligonucleotides). In some embodiments, the VLPs (or compositions thereof) are administered intramuscularly.

In some embodiments of the methods of eliciting an immune response or immunizing a subject, the subject is administered about 1 to about 25 µg of the VLPs containing an optimized HA protein. In particular examples, the subject is administered about 5 to about 20 µg of the VLPs, or about 10 to about 15 µg of the VLPs. In one specific non-limiting example, the subject is administered about 15 µg of the VLPs. However, one of skill in the art is capable of determining a therapeutically effective amount (for example an amount that provides protection against H1N1 influenza virus infection) of VLPs to administer to a subject.

IV. Optimized H1N1 Influenza HA Polypeptides and Polynucleotides

Provided herein are 11 different optimized H1N1 HA polypeptide sequences. H1N1 HA amino acid sequences were downloaded from the NCBI Influenza Virus Resource database. H1N1 HA proteins from 1134 isolates from 1918-2011 were used for generating consensus sequences. Example 1 describes the methods that were used to generate each consensus sequence (see also FIGS. 1-5).

COBRA METHOD 1
(SEQ ID NO: 1)
MKAKLLVLLCAFTATYADTICIGYHANNSTDTVDTVLEKNVTVTHSVNLLEDSHNGKLCRL

KGIAPLQLGNCSIAGWILGNPECESLFSKESWSYIVETPNSENGTCYPGYFADYEELREQLSS

VSSFERFEIFPKESSWPNHTVTKGVTASCSHNGKSSFYRNLLWLTEKNGSYPNLSKSYVNNK

EKEVLVLWGVHHPSNIGDQRAIYHTENAYVSVVSSHYSRRFTPEIAKRPKVRDQEGRINYY

WTLLEPGDTIIFEANGNLIAPWYAFALSRGFGSGIITSNASMDECDAKCQTPQGAINSSLPFQ

NVHPVTIGECPKYVRSTKLRMVTGLRNIPSIQSRGLFGAIAGFIEGGWTGMIDGWYGYHHQ

NEQGSGYAADQKSTQNAINGITNKVNSVIEKMNTQFTAVGKEFNKLERRMENLNKKVDDG

FLDIWTYNAELLVLLENERTLDFHDSNVKNLYEKVKSQLKNNAKEIGNGCFEFYHKCNNEC

MESVKNGTYDYPKYSEESKLNREKIDGVKLESMGVYQILAIYSTVASSLVLLVSLGAISFW

MCSNGSLQCRICI

COBRA METHOD 2
(SEQ ID NO: 2)
MKAKLLVLLCALTATDADTICIGYHANNSTDTVDTVLEKNVTVTHSVNLLEDSHNGKLCRL

KGIAPLQLGNCSIAGWILGNPECESLFSKKSWSYIAETPNSENGTCYPGYFADYEELREQLSS

VSSFERFEIFPKESSWPNHTVTKGVTAACSHKGKSSFYRNLLWLTEKNGSYPNLSKSYVNN

KEKEVLVLWGVHHPSNIGDQRAIYHTENAYVSVVSSHYNRRFTPEIAKRPKVRDQEGRINY

YWTLLEPGDTIIFEANGNLIAPWYAFALSRGFGSGIITSNASMDECDAKCQTPQGAINSSLPF

QNVHPVTIGECPKYVRSTKLRMVTGLRNIPSIQSRGLFGAIAGFIEGGWTGMIDGWYGYHH

QNEQGSGYAADQKSTQNAINGITNKVNSVIEKMNTQFTAVGKEFNKLEKRMENLNKKVDD

GFLDIWTYNAELLVLLENERTLDFHDSNVKNLYEKVKSQLKNNAKEIGNGCFEFYHKCNNE

CMESVKNGTYDYPKYSEESKLNREKIDGVKLESMGVYQILAIYSTVASSLVLLVSLGAISFW

MCSNGSLQCRICI

COBRA METHOD 3
(SEQ ID NO: 3)
MKAKLLVLLCAFTATYADTICIGYHANNSTDTVDTVLEKNVTVTHSVNLLEDSHNGKLCRL

KGIAPLQLGNCSVAGWILGNPECESLISKESWSYIVETPNPENGTCYPGYFADYEELREQLSS

VSSFERFEIFPKESSWPNHTVTKGVTASCSHNGKSSFYRNLLWLTEKNGLYPNLSKSYVNNK

EKEVLVLWGVHHPSNIGDQRALYHTENAYVSVVSSHYSRRFTPEIAKRPKVRDQEGRINYY

WTLLEPGDTIIFEANGNLIAPWYAFALSRGFGSGIITSNASMDECDAKCQTPQGAINSSLPFQ

NVHPVTIGECPKYVRSTKRMVTGLRNIPSIQSRGLFGAIAGFIEGGWTGMIDGWYGYHHQ

NEQGSGYAADQKSTQNAINGITNKVNSVIEKMNTQFTAVGKEFNKLERRMENLNKKVDDG

FLDIWTYNAELLVLLENERTLDFHDSNVKNLYEKVKSQLKNNAKEIGNGCFEFYHKCNNEC

MESVKNGTYDYPKYSEESKLNREKIDGVKLESMGVYQILAIYSTVASSLVLLVSLGAISFW

MCSNGSLQCRICI

COBRA METHOD 4
(SEQ ID NO: 4)
MKAKLLVLLCALTATDADTICIGYHANNSTDTVDTVLEKNVTVTHSVNLLEDSHNGKLCRL

KGIAPLQLGKCSIAGWILGNPECESLLSKKSWSYIAETPNSENGTCYPGYFADYEELREQLSS

VSSFERFEIFPKESSWPNHNVTKGVTASCSHKGKSSFYRNLLWLTEKNGSYPNLSKSYVNNK

EKEVLVLWGVHHPSNIGDQRTIYRTENAYVSVVSSNYNRRFTPEIAKRPKVRDQEGRINYY

WTLLEPGDTIIFEANGNLIAPWYAFALSRGFGSGIITSNASMDECDTKCQTPQGAINSSLPFQ

NVHPVTIGECPKYVRSTKLRMVTGLRNIPSIQSRGLFGAIAGFIEGGWTGMIDGWYGYHHQ

NEQGSGYAADQKSTQNAINGITNKVNSVIEKMNTQFTAVGKEFNKLEKRMENLNKKVDDG

```
FLDIWTYNAELLVLLENERTLDFHDSNVKNLYEKVKSQLKNNAKEIGNGCFEFYHKCNNEC

MESVKNGTYDYPKYSEESKLNREKIDGVKLESMGVYQILAIYSTVASSLVLLVSLGAISFW

MCSNGSLQCRICI
```

COBRA METHOD 5

(SEQ ID NO: 5)
```
MKAKLLVLLCTFTATDADTICIGYHANNSTDTVDTVLEKNVTVTHSVNLLEDSHNGKLCRL

KGIAPLQLGNCSIAGWILGNPECESLLSKKSWSYIVETPNSENGTCYPGDFIDYEELREQLSS

VSSFERFEIFPKESSWPNHTVTKGVTAACSHAGKSSFYRNLLWLTEKNGSYPNLSKSYVNN

KGKEVLVLWGVHHPSNIGDQQALYQTENAYVSVVSSHYNRKFTPEIAKRPKVRDQEGRIN

YYWTLLEPGDTIIFEANGNLIAPWYAFALSRGFGSGIITSNASMHECDTKCQTPQGAINSSLP

FQNIHPVTIGECPKYVRSTKLRMVTGLRNIPSIQSRGLFGAIAGFIEGGWTGMIDGWYGYHH

QNEQGSGYAADQKSTQNAINGITNKVNSVIEKMNTQFTAVGKEFNKLEKRMENLNKKVDD

GFLDIWTYNAELLVLLENERTLDFHDSNVKNLYEKVKSQLKNNAKEIGNGCFEFYHKCNNE

CMESVKNGTYDYPKYSEESKLNREKIDGVKLESMGVYQILAIYSTVASSLVLLVSLGAISFW

MCSNGSLQCRICI
```

COBRA METHOD 6

(SEQ ID NO: 6)
```
MKAKLLVLLCAFTATDADTICIGYHANNSTDTVDTVLEKNVTVTHSVNLLEDSHNGKLCKL

KGIAPLQLGKCSIAGWILGNPECESLLSKKSWSYIVETPNSENGTCYPGDFADYEELREQLSS

VSSFERFEIFPKESSWPNHTVTKGVTAACSHAGKSSFYRNLLWLTEKNGSYPNLSKSYVNN

KEKEVLVLWGVHHPSNIGDQRALYHTENAYVSVVSSHYNRRFTPEIAKRPKVRDQEGRINY

YWTLLEPGDTIIFEANGNLIAPWYAFALSRGFGSGIITSNASMDECDAKCQTPQGAINSSLPF

QNVHPVTIGECPKYVRSTKLRMVTGLRNIPSIQSRGLFGAIAGFIEGGWTGMIDGWYGYHH

QNEQGSGYAADQKSTQNAINGITNKVNSVIEKMNTQFTAVGKEFNKLERRMENLNKKVDD

GFLDIWTYNAELLVLLENERTLDFHDSNVKNLYEKVKSQLKNNAKEIGNGCFEFYHKCNNE

CMESVKNGTYDYPKYSEESKLNREKIDGVKLESMGVYQILAIYSTVASSLVLLVSLGAISFW

MCSNGSLQCRICI
```

COBRA METHOD 5 DEGLYCOSYLATED (SEQ ID NO: 7)
```
MKAKLLVLLCTFTATDADTICIGYHANNSTDTVDTVLEKNVTVTHSVNLLEDSHNGKLCRL

KGIAPLQLGNCAIAGWILGNPECESLLSKKSWSYIVETPNSENGTCYPGDFIDYEELREQLSS

VSSFERFEIFPKESSWPNHAVTKGVTAACSHAGKSSFYRNLLWLTEKNGSYPNLAKSYVNN

KGKEVLVLWGVHHPSNIGDQQALYQTENAYVSVVSSHYNRKFTPEIAKRPKVRDQEGRIN

YYWTLLEPGDTIIFEANGNLIAPWYAFALSRGFGSGIITSNAAMHECDTKCQTPQGAINSSLP

FQNIHPVTIGECPKYVRSTKLRMVTGLRNIPSIQSRGLFGAIAGFIEGGWTGMIDGWYGYHH

QNEQGSGYAADQKSTQNAINGITNKVNSVIEKMNTQFTAVGKEFNKLEKRMENLNKKVDD

GFLDIWTYNAELLVLLENERTLDFHDSNVKNLYEKVKSQLKNNAKEIGNGCFEFYHKCNNE

CMESVKNGTYDYPKYSEESKLNREKIDGVKLESMGVYQILAIYSTVASSLVLLVSLGAISFW

MCSNGSLQCRICI
```

1918-1957 COBRA (SEQ ID NO: 8)
```
MKARLLVLLCALAATDADTICIGYHANNSTDTVDTVLEKNVTVTHSVNLLEDSHNGKLCR

LKGIAPLQLGKCNIAGWILG

-continued

KGKEVLVLWGVHHPSNIDDQQTLYQKENAYVSVVSSNYNRRFTPEIAERPKVRGQAGRMN

YYWTLLEPGDTIIFEANGNLIAPWYAFALSRGFGSGIITSNASMHECDTKCQTPQGAINSSLP

FQNIHPVTIGECPKYVRSTKLRMVTGLRNIPSIQSRGLFGAIAGFIEGGWTGMIDGWYGYHH

QNEQGSGYAADQKSTQNAINGITNKVNSVIEKMNTQFTAVGKEFNNLEKRMENLNKKVDD

GFLDIWTYNAELIVLLENERTLDFHDSNVKNLYEKVKSQLRNNAKEIGNGCFEFYHKCDNE

CMESVKNGTYDYPKYSEESKLNREKIDGVKLESMGVYQILAIYSTVASSLVLLVSLGAISFW

MCSNGSLQCRICI 1977-2005 COBRA (SEQ ID NO: 9)

MKAKLLVLLCAFTATDADTICIGYHANNSTDTVDTVLEKNVTVTHSVNLLEDSHNGKLCRL

KGIAPLQLGNCSIAGWILGNPECESLFSKKSWSYIAETPNSENGTCYPGYFADYEELREQLSS

VSSFERFEIFPKESSWPNHTVTKGVTASCSHKGKSSFYRNLLWLTEKNGSYPNLSKSYVNNK

EKEVLVLWGVHHPSNIGDQRAIYHTENAYVSVVSSHYNRRFTPEIAKRPKVRDQEGRINYY

WTLLEPGDTIIFEANGNLIAPWYAFALSRGFGSGIITSNASMDECDAKCQTPQGAINSSLPFQ

NVHPVTIGECPKYVRSTKLRMVTGLRNIPSIQSRGLFGAIAGFIEGGWTGMIDGWYGYHHQ

NEQGSGYAADQKSTQNAINGITNKVNSVIEKMNTQFTAVGKEFNKLERRMENLNKKVDDG

FLDIWTYNAELLVLLENERTLDFHDSNVKNLYEKVKSQLKNNAKEIGNGCFEFYHKCNNEC

MESVKNGTYDYPKYSEESKLNREKIDGVKLESMGVYQILAIYSTVASSLVLLVSLGAISFW

MCSNGSLQCRICI

HUMAN SWINE COBRA (SEQ ID NO: 10)

MKAILLVLLCTFAATNADTLCIGYHANNSTDTVDTVLEKNVTVTHSVNLLEDKHNGKLCK

LKGIAPLHLGKCNIAGWLLGNPECELLLTASSWSYIVETSNSDNGTCYPGDFIDYEELREQLS

SVSSFERFEIFPKTSSWPNHETNKGVTAACPYAGASSFYRNLIWLVKKGNSYPKLSKSYVNN

KGKEVLVLWGIHHPPTSTDQQSLYQNADAYVFVGSSKYNRKFKPEIAARPKVRDQAGRMN

YYWTLIEPGDTITFEATGNLVVPRYAFAMNRGSGSGIIISDAPVHDCNTKCQTPKGAINTSLP

FQNIHPVTIGECPKYVKSTKLRMATGLRNIPSIQSRGLFGAIAGFIEGGWTGMIDGWYGYHH

QNEQGSGYAADQKSTQNAIDGITNKVNSVIEKMNTQFTAVGKEFNHLEKRIENLNKKVDD

GFLDIWTYNAELLVLLENERTLDFHDSNVKNLYEKVRSQLKNNAKEIGNGCFEFYHKCDDT

CMESVKNGTYDYPKYSEESKLNREEIDGVKLESTRIYQILAIYSTVASSLVLLVSLGAISFWM

CSNGSLQCRICI

SWINE COBRA (SEQ ID NO: 11)

MKAILLVLLCTFTAANADTLCIGYHANNSTDTVDTVLEKNVTVTHSVNLLEDRHNGKLCKL

GGIAPLHLGKCNIAGWLLGNPECELLLTASSWSYIVETSNSDNGTCYPGDFINYEELREQLSS

VSSFERFEIFPKASSWPNHETNRGVTAACPYAGANSFYRNLIWLVKKGNSYPKLSKSYVNN

KGKEVLVLWGIHHPPTSTDQQSLYQNADAYVFVGSSKYNRKFKPEIAARPKVRGQAGRMN

YYWTLLEPGDTITFEATGNLVVPRYAFAMNRGSGSGIIISDAPVHDCNTKCQTPKGAINTSLP

FQNIHPVTIGECPKYVKSTKLRMATGLRNIPSIQSRGLFGAIAGFIEGGWTGMIDGWYGYHH

QNEQGSGYAADQKSTQNAIDGITNKVNSVIEKMNTQFTAVGKEFNHLEKRIENLNKKVDD

-continued
```
GFLDVWTYNAELLVLLENERTLDFHDSNVKNLYEKVRSQLRNNAKEIGNGCFEFYHKCDD

TCMESVKNGTYDYPKYSEESKLNREEIDGVKLESTRIYQILAIYSVASSLVLLVSLGAISFW

MCSNGSLQCRICI

Consensus of SEQ ID NOs: 1-11
                                                    (SEQ ID NO: 12)
MKAXLLVLLCXXXAXXADTXCIGYHANNSTDTVDTVLEKNVTVTHSVNLLEDXHNGKLC

XLXGIAPLXLGXCXXAGWXLGNPECEXLXXXXSWSYIXETXNXXNGTCYPGXFXXYEELR

EQLSSVSSFERFEIFPKXSSWPXHXXXXGVTAXCXXXGXXSFYRNLXWLXXKXXXYPXLX

XSYVNNKXKEVLVLWGXHHPXXXXDQXXXYXXXXAYVXVXSSXYXRXFXPEIAXRPKV

RXQXGRXNYYWTLXEPGDTIXFEAXGNLXXPXYAFAXXRGXGSGIIXSXAXXXXCXXKCQ

TPXGAINXSLPFQNXHPVTIGECPKYVXSTKLRMXTGLRNIPSIQSRGLFGAIAGFIEGGWTG

MIDGWYGYHHQNEQGSGYAADQKSTQNAIXGITNKVNSVIEKMNTQFTAVGKEFNXLEXR

XENLNKKVDDGFLDXWTYNAELLVLLENERTLDFHDSNVKNLYEKVXSQLXNNAKEIGN

GCFEFYHKCXXXDMESVKNGTYDYPKYSEESKLNREXIDGVKLESXXXXYQILAIYSTVASS

LVLLVSLGAISFWMCSNGSLQCRICI
```

In some embodiments disclosed herein, the HA polypeptides lack the N-terminal methionine residue. Thus, in some examples, provided are HA polypeptides comprising residues 2-566 of any one of SEQ ID NOs: 1-12.

The COBRA amino acid sequences can be reverse translated and optimized for expression in mammalian cells, including codon usage and RNA optimization (GeneArt; Regensburg, Germany). The optimized nucleic acid sequences can be inserted into an appropriate expression vector, such as the pTR600 expression vector (U.S. Patent Application Publication No. 2002/0106798; Ross et al., *Nat Immunol.* 1(2): 102-103, 2000; Green et al., *Vaccine* 20:242-248, 2001).

The optimized nucleic acid sequence of the COBRA HA sequence of Method 1 is (SEQ ID NO: 13):

```
AAGCTTATGAAGGCCAAGCTGCTGGTGCTGCTGTGCGCCTTCACAGCCAC

CTACGCCGACACCATCTGCATCGGCTACCACGCCAACAACAGCACCGACA

CCGTGGATACCGTGCTGGAAAAGAACGTGACCGTGACCCACAGCGTGAAC

CTGCTGGAAGATAGCCACAACGGCAAGCTGTGCCGGCTGAAGGGAATCGC

CCCTCTGCAGCTGGGCAACTGCTCTATCGCCGGCTGGATTCTGGGCAACC

CCGAGTGCGAGAGCCTGTTCAGCAAAGAGTCCTGGTCCTACATCGTGGAA

ACCCCCAACAGCGAGAACGGCACCTGTTACCCCGGCTACTTCGCCGACTA

CGAGGAACTGCGGGAACAGCTGAGCAGCGTGTCCAGCTTCGAGAGATTCG

AGATTTTCCCCAAGAGAGCAGCTGGCCCAACCACACCGTGACCAAAGGC

GTGACCGCCTCCTGCTCCCACAATGGCAAGAGCAGCTTCTACAGAAACCT

GCTGTGGCTGACCGAGAAGAACGGCAGCTACCCCAACCTGAGCAAGAGCT

ACGTGAACAACAAGAAAAGAGGTGCTGGTGCTGTGGGCGTGCACCAC

CCTAGCAACATCGGCGACCAGCGGGCCATCTACCACACCGAGAATGCCTA

CGTGTCCGTGGTGTCCAGCCACTACAGCAGACGGTTCACCCCCGAGATCG

CCAAGAGGCCCAAAGTGCGGGACCAGGAAGGCCGGATCAACTACTACTGG

ACACTGCTGGAACCCGGCGATACCATCATCTTCGAGGCCAACGGCAACCT

GATCGCCCCTTGGTACGCCTTCGCCCTGAGCAGAGGCTTTGGCAGCGGCA

TCATCACCAGCAACGCCAGCATGGACGAGTGCGACGCCAAGTGCCAGACA

CCTCAGGGCGCCATCAATAGCAGCCTGCCCTTCCAGAACGTGCACCCCGT

GACCATCGGCGAGTGCCCCAAATACGTGCGGAGCACCAAGCTGCGGATGG

TCACCGGCCTGAGAAACATCCCCAGCATCCAGAGCAGGGGCCTGTTCGGA

GCCATTGCCGGCTTTATCGAGGGCGGCTGGACCGGCATGATCGACGGGTG

GTACGGCTATCACCACCAGAACGAGCAGGGCAGCGGCTACGCCGCCGATC

AGAAGTCTACCCAGAACGCCATCAACGGCATCACCAACAAAGTGAACAGC

GTGATCGAGAAGATGAACACCCAGTTCACCGCCGTGGGCAAGAGTTCAA

CAAGCTGGAACGGCGGATGGAAAACCTGAACAAGAAGGTGGACGACGGCT

TCCTGGACATCTGGACCTACAACGCCGAACTGCTGGTGCTGCTGGAAAAC

GAGCGGACCCTGGACTTCCACGACAGCAACGTGAAGAACCTGTACGAGAA

AGTGAAGTCCCAGCTGAAGAACAACGCCAAAGAGATCGGCAACGGCTGCT

TCGAGTTCTACCACAAGTGCAACAACGAGTGCATGGAAAGCGTGAAGAAT

GGCACCTACGACTACCCCAAGTACAGCGAGGAAAGCAAGCTGAACCGCGA

GAAGATCGACGGCGTGAAGCTGGAATCCATGGGCGTGTACCAGATCCTGG

CCATCTATAGCACCGTGGCCAGCAGCCTGGTGCTGCTGGTGTCTCTGGGC

GCCATCAGCTTTTGGATGTGCAGCAACGGCAGCCTGCAGTGCCGGATCTG

TATCGGCAGCATCGGATCC
```

V. Influenza

Influenza viruses are segmented negative-strand RNA viruses that belong to the Orthomyxoviridae family. There are three types of Influenza viruses, A, B and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as H5N1, cause systemic infections in poultry in which mortality may reach 100%. Animals infected with influenza A often act as a reservoir for the influenza viruses and certain subtypes have been shown to cross the species barrier to humans.

Influenza A viruses can be classified into subtypes based on allelic variations in antigenic regions of two genes that encode surface glycoproteins, namely, hemagglutinin (HA) and neuraminidase (NA) which are required for viral attachment and cellular release. Currently, sixteen subtypes of HA (H1-H16) and nine NA (N1-N9) antigenic variants are known for influenza A virus. Previously, only three subtypes were known to circulate in humans (H1N1, H1N2, and H3N2). However, in recent years, the pathogenic H5N1 subtype of avian influenza A has been reported to cross the species barrier and infect humans as documented in Hong Kong in 1997 and 2003, leading to the death of several patients.

In animals, most influenza A viruses cause mild localized infections of the respiratory and intestinal tract. However, highly pathogenic influenza A strains, such as H5N1, cause systemic infections in poultry in which mortality may reach 100%. In 2009, H1N1 influenza was the most common cause of human influenza. A new strain of swine-origin H1N1 emerged in 2009 and was declared pandemic by the World Health Organization. This strain was referred to as "swine flu." H1N1 influenza A viruses were also responsible for the Spanish flu pandemic in 1918, the Fort Dix outbreak in 1976, and the Russian flu epidemic in 1977-1978.

The influenza A virus genome encodes nine structural proteins and one nonstructural (NS1) protein with regulatory functions. The influenza virus segmented genome contains eight negative-sense RNA (nsRNA) gene segments (PB2, PB1, PA, NP, M, NS, HA and NA) that encode at least ten polypeptides, including RNA-directed RNA polymerase proteins (PB2, PB1 and PA), nucleoprotein (NP), neuraminidase (NA), hemagglutinin (subunits HA1 and HA2), the matrix proteins (M1 and M2) and the non-structural proteins (NS1 and NS2) (Krug et al., In "The Influenza Viruses," R. M. Krug, ed., Plenum Press, N.Y., 1989, pp. 89 152).

Influenza virus' ability to cause widespread disease is due to its ability to evade the immune system by undergoing antigenic change, which is believed to occur when a host is infected simultaneously with both an animal influenza virus and a human influenza virus. During mutation and reassortment in the host, the virus may incorporate an HA and/or NA surface protein gene from another virus into its genome, thereby producing a new influenza subtype and evading the immune system.

HA is a viral surface glycoprotein generally comprising approximately 560 amino acids and representing 25% of the total virus protein. It is responsible for adhesion of the viral particle to, and its penetration into, a host cell in the early stages of infection. Cleavage of the virus HA0 precursor into the HA1 and HA2 sub-fragments is a necessary step in order for the virus to infect a cell. Thus, cleavage is required in order to convert new virus particles in a host cell into virions capable of infecting new cells. Cleavage is known to occur during transport of the integral HA0 membrane protein from the endoplasmic reticulum of the infected cell to the plasma membrane. In the course of transport, hemagglutinin undergoes a series of co- and post-translational modifications including proteolytic cleavage of the precursor HA into the amino-terminal fragment HA1 and the carboxy terminal HA2. One of the primary difficulties in growing influenza strains in primary tissue culture or established cell lines arises from the requirement for proteolytic cleavage activation of the influenza hemagglutinin in the host cell.

Although it is known that an uncleaved HA can mediate attachment of the virus to its neuraminic acid-containing receptors on a cell surface, it is not capable of the next step in the infectious cycle, which is fusion. It has been reported that exposure of the hydrophobic amino terminus of HA2 by cleavage is required so that it can be inserted into the target cell, thereby forming a bridge between virus and target cell membrane. This process is followed by fusion of the two membranes and entry of the virus into the target cell.

Proteolytic activation of HA involves cleavage at an arginine residue by a trypsin-like endoprotease, which is often an intracellular enzyme that is calcium dependent and has a neutral pH optimum. Since the activating proteases are cellular enzymes, the infected cell type determines whether the HA is cleaved. The HA of the mammalian influenza viruses and the nonpathogenic avian influenza viruses are susceptible to proteolytic cleavage only in a restricted number of cell types. On the other hand, HA of pathogenic avian viruses among the H5 and H7 subtypes are cleaved by proteases present in a broad range of different host cells. Thus, there are differences in host range resulting from differences in hemagglutinin cleavability which are correlated with the pathogenic properties of the virus.

Neuraminidase (NA) is a second membrane glycoprotein of the influenza viruses. The presence of viral NA has been shown to be important for generating a multi-faceted protective immune response against an infecting virus. For most influenza A viruses, NA is 413 amino acid in length, and is encoded by a gene of 1413 nucleotides. Nine different NA subtypes have been identified in influenza viruses (N1, N2, N3, N4, N5, N6, N7, N8 and N9), all of which have been found among wild birds. NA is involved in the destruction of the cellular receptor for the viral HA by cleaving terminal neuraminic acid (also called sialic acid) residues from carbohydrate moieties on the surfaces of infected cells. NA also cleaves sialic acid residues from viral proteins, preventing aggregation of viruses. Using this mechanism, it is hypothesized that NA facilitates release of viral progeny by preventing newly formed viral particles from accumulating along the cell membrane, as well as by promoting transportation of the virus through the mucus present on the mucosal surface. NA is an important antigenic determinant that is subject to antigenic variation.

In addition to the surface proteins HA and NA, influenza virus comprises six additional internal genes, which give rise to eight different proteins, including polymerase genes PB1, PB2 and PA, matrix proteins M1 and M2, nucleoprotein (NP), and non-structural proteins NS1 and NS2 (Horimoto et al., *Clin Microbiol Rev.* 14(1):129-149, 2001).

In order to be packaged into progeny virions, viral RNA is transported from the nucleus as a ribonucleoprotein (RNP) complex composed of the three influenza virus polymerase proteins, the nucleoprotein (NP), and the viral RNA, in association with the influenza virus matrix 1 (M1) protein and nuclear export protein (Marsh et al., *J Virol,* 82:2295-2304, 2008). The M1 protein that lies within the envelope is thought to function in assembly and budding. A limited number of M2 proteins are integrated into the virions (Zebedee, *J. Virol.* 62:2762-2772, 1988). They form tetramers having H+ ion channel activity, and when activated by the low pH in endosomes, acidify the inside of the virion, facilitating its uncoating (Pinto et al., *Cell* 69:517-528, 1992). Amantadine is an anti-influenza drug that prevents viral infection by interfering with M2 ion channel activity, thus inhibiting virus uncoating.

NS1, a nonstructural protein, has multiple functions, including regulation of splicing and nuclear export of cellular mRNAs as well as stimulation of translation. The major function of NS1 seems to be to counteract the interferon activity of the host, since an NS1 knockout virus was viable although it grew less efficiently than the parent virus in interferon-nondefective cells (Garcia-Sastre, *Virology* 252: 324-330, 1998).

NS2 has been detected in virus particles (Richardson et al., *Arch. Virol.* 116:69-80, 1991; Yasuda et al., *Virology* 196:249-255, 1993). The average number of NS2 proteins in a virus particle was estimated to be 130-200 molecules. An in vitro binding assay shows direct protein-protein contact between M1 and NS2. NS2-M1 complexes have also been detected by immunoprecipitation in virus-infected cell lysates. The NS2 protein is thought to play a role in the export of RNP from the nucleus through interaction with M1 protein (Ward et al., *Arch. Virol.* 140:2067-2073, 1995).

VI. Influenza VLPs and Administration Thereof

Influenza VLPs comprising an optimized HA (such as the HA having the amino acid sequence set forth as any one of SEQ ID NOs: 1-11) are provided herein. The influenza VLPs are generally made up of the HA, NA and M1 proteins. The production of influenza VLPs has been described in the art and is within the abilities of one of ordinary skill in the art. For example, influenza VLPs can be produced by transfection of host cells with plasmids encoding the HA, NA and M1 proteins. After incubation of the transfected cells for an appropriate time to allow for protein expression (such as for approximately 72 hours), VLPs can be isolated from cell culture supernatants. Example 2 below provides an exemplary protocol for purifying influenza VLPs from cell supernatants. In this example, VLPs are isolated by low speed centrifugation (to remove cell debris), vacuum filtration and ultracentrifugation through 20% glycerol.

The influenza VLPs disclosed herein can be used as influenza vaccines to elicit a protective immune response against H1N1 influenza viruses.

Influenza VLPs, or compositions thereof, can be administered to a subject by any of the routes normally used for introducing recombinant virus into a subject. Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

Influenza VLPs, or compositions thereof, are administered in any suitable manner, such as with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose administered to a subject in the context of the present disclosure should be sufficient to induce a beneficial therapeutic response in a subject over time, or to inhibit or prevent H1N1 influenza virus infection. The dose required will vary from subject to subject depending on the species, age, weight and general condition of the subject, the severity of the infection being treated, the particular composition being used and its mode of administration. An appropriate dose can be determined by one of ordinary skill in the art using only routine experimentation.

Provided herein are pharmaceutical compositions which include a therapeutically effective amount of the influenza VLPs alone or in combination with a pharmaceutically acceptable carrier. Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

The influenza VLPs described herein can be administered alone or in combination with other therapeutic agents to enhance antigenicity. For example, the influenza VLPs can be administered with an adjuvant, such as Freund incomplete adjuvant or Freund's complete adjuvant.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, *J. Surg. Oncol.* 68(2): 122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcystein-lyseryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

Although administration of VLPs containing an optimized HA protein is exemplified herein, one of skill in the art would understand that it is also possible to administer the optimized influenza HA protein itself (in the absence of a viral particle) or as a fusion protein to elicit an immune response in a subject.

The following examples are provided to illustrate certain particular features and/or embodiments. These examples should not be construed to limit the disclosure to the particular features or embodiments described.

EXAMPLES

Example 1: Generation of COBRA Sequences for H1N1 Influenza

Influenza A H1N1 HA amino acid sequences were downloaded from the NCBI Influenza Virus Resource database. H1N1 HA proteins from 1134 isolates from 1918-2011 were used for generating consensus sequences. Eleven different consensus sequences (SEQ ID NOs: 1-11) were generated using the following methods:

1. COBRA Method 1 (1918-2005)
Sequences (456) were organized by date of isolation and eight primary consensus sequences were generated using isolates from 1918-1934 (8), 1935-1947 (13), 1948-1957 (12), 1977-1983 (68), 1984-1986 (9), 1987-1991 (12), 1992-1999 (59) and 2000-2005 (263). Four secondary consensus sequences were generated by grouping the primary consensus sequences by date, as shown in FIG. 1. The final consensus sequence (the third layer consensus; SEQ ID NO: 1) was generated by alignment of the four secondary consensus sequences.

Figure 2:
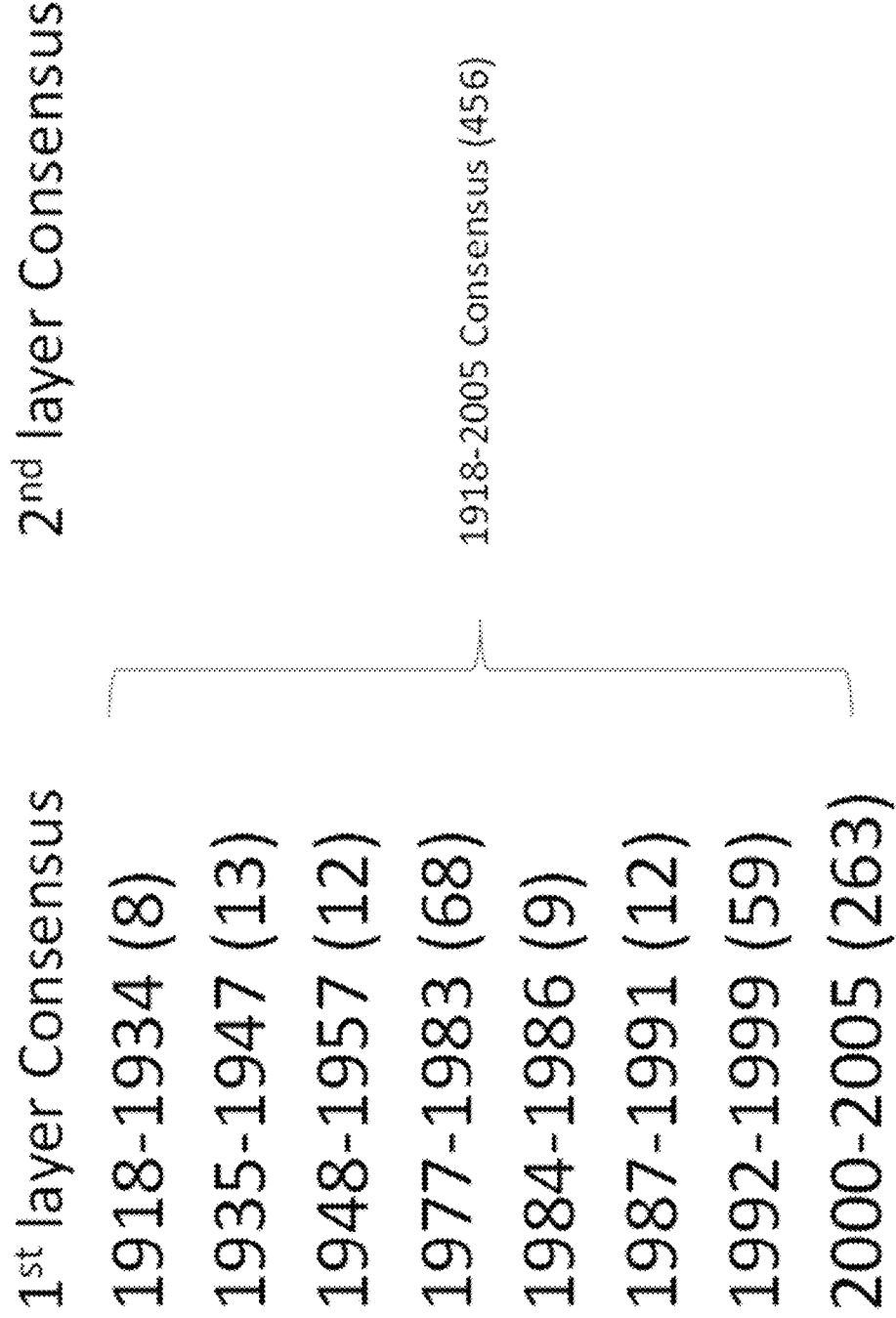
FIG. 2 is a schematic of the process used to generate an H1N1 HA consensus sequence according to Method 2.

2. COBRA Method 2 (1918-2005)
As with method 1, sequences (456) were organized by date of isolation to generate eight primary consensus sequences. The final consensus sequence (SEQ ID NO: 2) was generated by aligning the eight primary consensus sequences, as illustrated in FIG. 2.

3. COBRA Method 3 (1918-2005)
The consensus sequence (SEQ ID NO: 3) was generated by alignment of 456 H1N1 virus isolates from 1918-2005.

Figure 3:
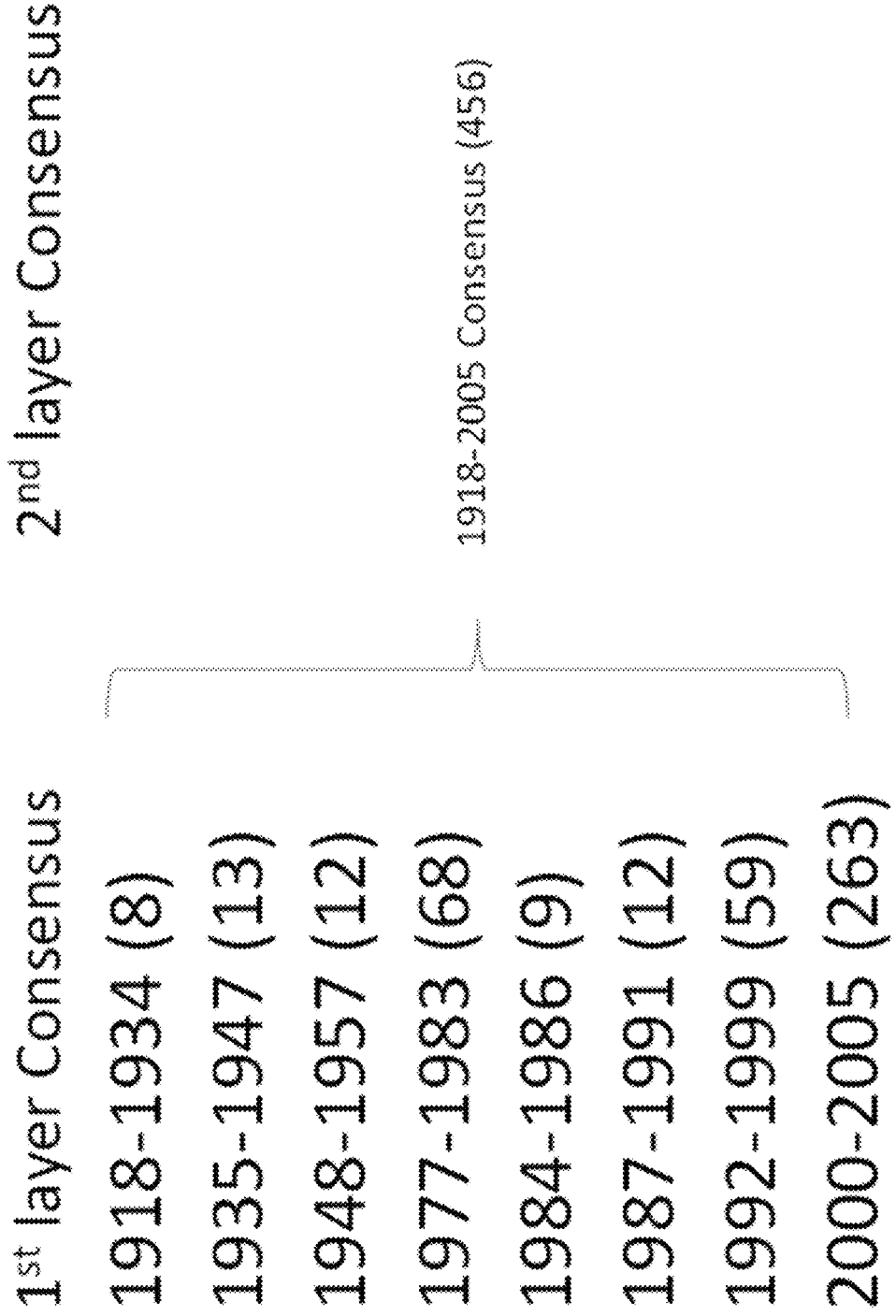
FIG. 3 is a schematic of the process used to generate an H1N1 HA consensus sequence according to Method 4.

4. COBRA Method 4 (1918-2005)
Sequences (456) were organized by date of isolation and ten primary consensus sequences were generated using isolates from 1918-1933 (6), 1934-1946 (15), 1947-1956 (12), 1957-1977 (8), 1978-1980 (17), 1981-1985 (49), 1986-1990 (14), 1991-1995 (27), 1996-1998 (27) and 1999-2005 (281), as shown in FIG. 3. The final consensus sequence (SEQ ID NO: 4) was generated by alignment of the ten primary consensus sequences.

Figure 4:
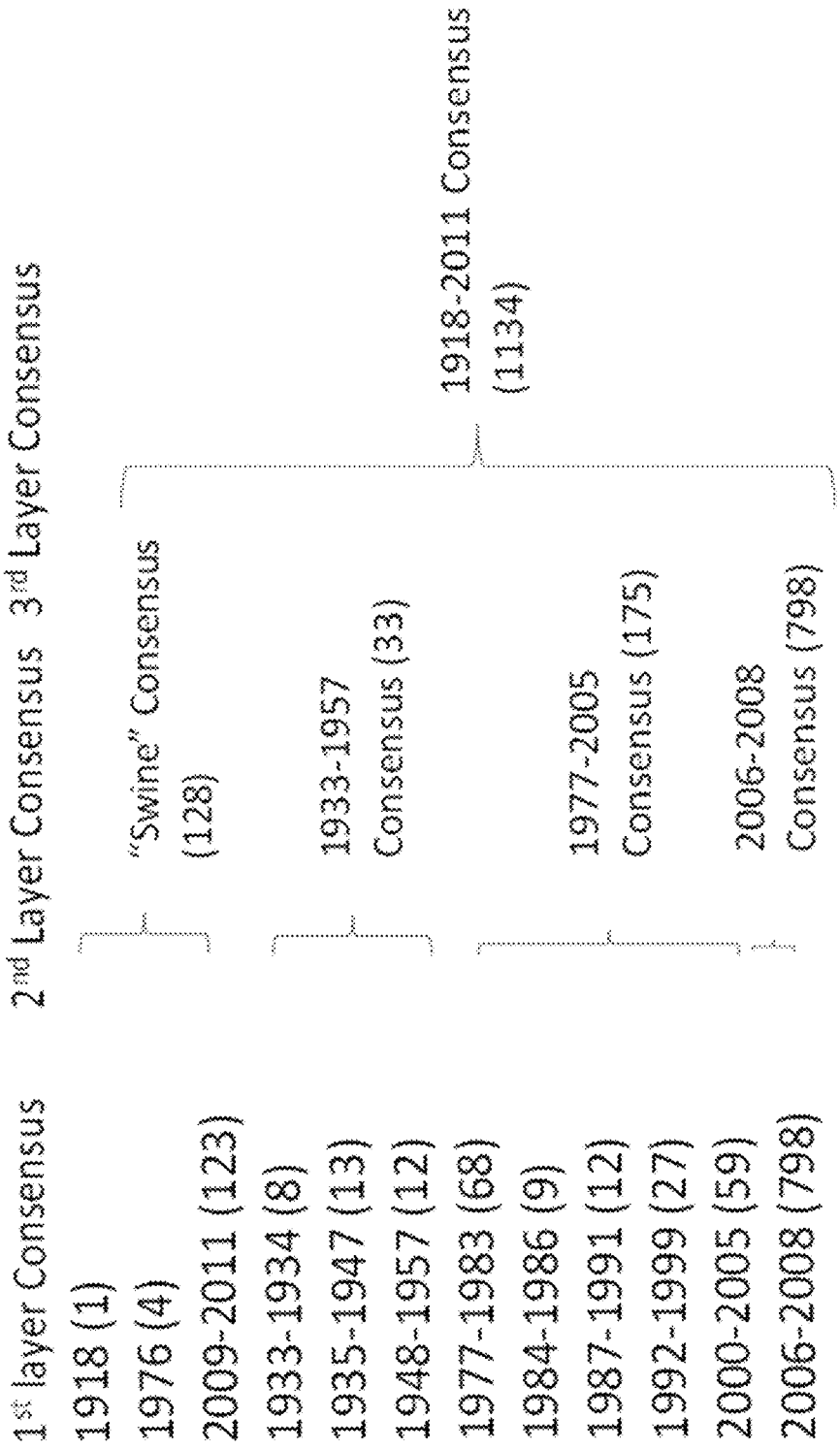
FIG. 4 is a schematic of the process used to generate an H N1 HA consensus sequence according to Method 5.

5. COBRA Method 5 (1918-2011)
Sequences (1134) were organized by date of isolation and 12 primary consensus sequences were generated using isolates from 1918 (1), 1976 (4), 2009-2011 (123), 1933-1934 (8), 1935-1947 (13), 1948-1957 (12), 1977-1983 (68), 1984-1986 (9), 1987-1991 (12), 1992-1999 (27), 2000-2005 (59) and 2006-2008 (798). Four secondary consensus sequences were generated by grouping the primary consensus sequences according to "swine" sequences or by date, as shown in FIG. 4. The final consensus sequence (the third layer consensus; SEQ ID NO: 5) was generated by alignment of the four secondary consensus sequences.

Figure 5:
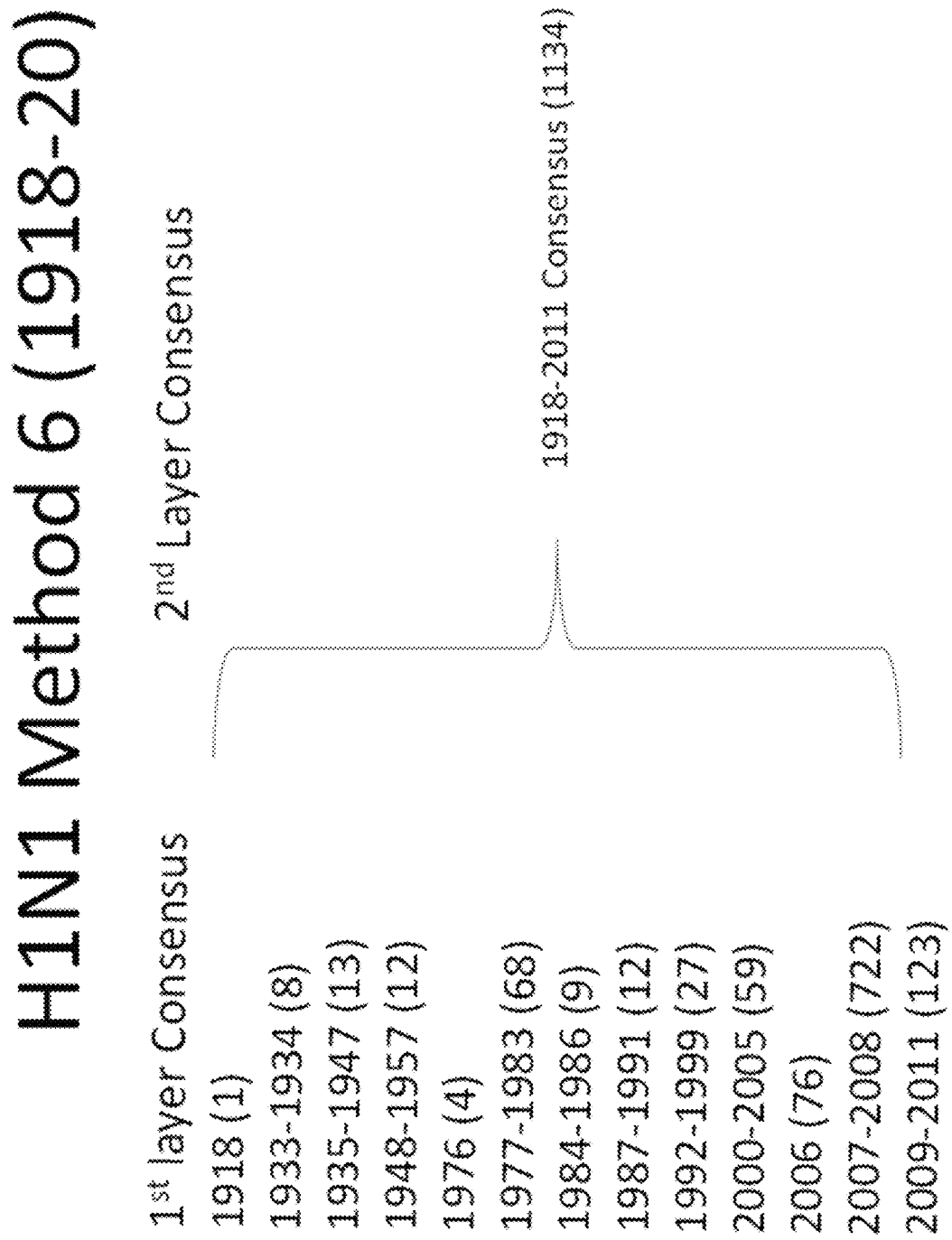
FIG. 5 is a schematic of the process used to generate an H1N1 HA consensus sequence according to Method 6.

6. COBRA Method 6
Sequences (1134) were organized by date of isolation and 13 primary consensus sequences were generated using isolates from 1918 (1), 1933-1934 (8), 1935-1947 (13), 1948-1957 (12), 1976 (4), 1977-1983 (68), 1984-1986 (9), 1987-1991 (12), 1992-1999 (27), 2000-2005 (59), 2006 (76), 2007-2008 (722) and 2009-2011 (123), as shown in FIG. 5. The final consensus sequence (SEQ ID NO: 6) was generated by alignment of the 13 primary consensus sequences.

7. COBRA Method 5 Deglycosylated
This sequence (SEQ ID NO: 7) was generated by altering the Method 5 consensus sequence (SEQ ID NO: 5) to remove predicted glycosylation sites.

8. 1918-1957 Cobra
This sequence (SEQ ID NO: 8) was generated by alignment of H1N1 isolates from 1918-1957.

9. 1977-2005 Cobra
This sequence (SEQ ID NO: 9) was generated by alignment of H1N1 isolates from 1977-2005.

10. Human Swine COBRA
This sequence (SEQ ID NO: 10) was generated by alignment of H1N1 human swine influenza isolates. This sequence was aligned using consensus sequences from 1918, 1976 and 2009-2011.

11. Swine COBRA
This sequence (SEQ ID NO: 11) was generated by alignment of H1N1 swine influenza isolates. This sequence was aligned using swine sequences from 1930-2010.

The COBRA amino acid sequence generated according to Method 1 was reverse translated and optimized for expression in mammalian cells, including codon usage and RNA optimization (GeneArt; Regensburg, Germany). The optimized nucleic acid sequence is set forth herein as SEQ ID NO: 13. The remaining COBRA sequences will also be reverse translated and optimized for expression in mammalian cells. The optimized nucleic acid sequences will be inserted into the pTR600 expression vector (U.S. Patent Application Publication No. 2002/0106798; Ross et al., *Nat Immunol.* 1(2):102-103, 2000; Green et al., *Vaccine* 20:242-248, 2001).

Example 2: Preparation of and Immunization with Influenza VLPs

The following methods can be used to produce and characterize influenza VLPs comprising an optimized HA.

Exemplary methods for immunization of mice, ferrets and macaques are also described below (see also, Giles and Ross, *Vaccine* 29(16):3043-3054, 2011).

Vaccine Preparation 293T cells are transiently transfected with plasmids expressing M1, NA and an optimized HA, and incubated for 72 hours at 37° C. The M1, NA and HA coding sequences can be codon-optimized for expression in mammalian cells. Supernatants are collected and cell debris is removed by low speed centrifugation followed by vacuum filtration through a 0.22 μm sterile filter. VLPs are purified via ultracentrifugation (100,000×g through 20% glycerol, weight per volume) for 4 hours at 4° C. The pellets are subsequently resuspended in PBS pH 7.2 and stored in single use aliquots at −80° C. until use. Total protein concentration is determined by Micro BCA™ Protein Assay Reagent Kit (Pierce Biotechnology, Rockford, Ill., USA).

Dose Determination

HA specific content can be determined by western blot and densitometry. Purified recombinant COBRA HA and purified VLPs are prepared in standard total protein amounts and are electrophoresed on a 10% SDS-PAGE gel and transferred to a PVDF membrane. The blot is probed with mouse polyclonal antisera from influenza infected mice and the HA-antibody complexes are detected using a goat anti-mouse IgG conjugated to horseradish peroxidase (HRP) (Southern Biotech; Birmingham, Ala., USA). HRP is detected by chemiluminescent substrate (Pierce Biotechnology; Rockford Ill., USA) and exposed to X-ray film (ThermoFisher, Pittsburgh, Pa., USA). Density of bands is determined using ImageJ software (NIH). Density of recombinant HA bands is used to calculate a standard curve and the density of the purified VLPs is interpolated using the results from the recombinant HA.

Mouse Studies

BALB/c mice (*Mus musculis*, females, 6-8 weeks old) can be purchased from Harlan Sprague Dawley (Indianapolis, Ind., USA). Mice are housed in microisolator units and allowed free access to food and water and are cared for under USDA guidelines for laboratory animals. Mice are vaccinated with one of three doses of purified COBRA HA VLPs (1.5 μg, 0.3 μg or 0.06 μg), based upon HA content from a densitometry assay, via intramuscular injection at week 0 and then boosted with the same dose at week 3. Vaccines at each dose are formulated with alum adjuvant (Imject Alum, Pierce Biotechnology; Rockford, Ill., USA), CpG oligonucleotides, or vehicle alone. Fourteen to twenty-one days after each vaccination, blood is collected from anesthetized mice via the retro-orbital plexus and transferred to a microfuge tube. Tubes are centrifuged and sera is removed and frozen at −80±5° C. Hemagglutination inhibition (HAI) serum antibody titer for each vaccine group is determined at week 5 using representative reassortant viruses or COBRA HA VLPs.

Three weeks after final vaccination, mice are challenged intranasally with a highly pathogenic H1N1 virus in a volume of 50 μl. After infection, mice are monitored daily for weight loss, disease signs and death for 14 days after infection. Individual body weights, sickness scores (Toapanta and Ross, *Respiratory Research* 10(1):112, 2009) and death are recorded for each group on each day after inoculation.

Ferret Studies

Fitch ferrets (*Mustela putorius furo*, female, 6-12-months of age), influenza naïve and de-scented, can be purchased from Marshall Farms (Sayre, Pa., USA). Ferrets are pair housed in stainless steel cages (Shor-line, Kansas City, Kans., USA) containing Sani-chips Laboratory Animal Bedding (P. J. Murphy Forest Products, Montville, N.J., USA). Ferrets are provided with Teklad Global Ferret Diet (Harlan Teklad, Madison, Wis., USA) and fresh water ad libitum. The COBRA HA VLPs are diluted in PBS, pH 7.2 to achieve final concentration. Ferrets are vaccinated with one of two doses of purified COBRA VLPs (15 μg, 3 μg), based upon HA content as determined by densitometry assay, via intramuscular injection in the quadriceps muscle in a volume of 0.25 ml at week 0 and then boosted with the same dose at week 3. Vaccines are stored at −80° C. prior to use and formulated with alum adjuvant (Imject Alum; Pierce Biotechnology, Rockford, Ill., USA) immediately prior to use. Animals are monitored for adverse events including weight loss, temperature, decrease in activity, nasal discharge, sneezing and diarrhea weekly during the vaccination regimen. Prior to vaccination, animals are confirmed by HAI assay to be seronegative for circulating influenza A and influenza B viruses. Fourteen to twenty-one days after each vaccination, blood is collected from anesthetized ferrets via the anterior vena cava and transferred to a microfuge tube. Tubes are centrifuged and sera is removed and frozen at −80±5° C. HAI serum antibody titer for each vaccine group is determined at week 5 using representative reassortant viruses or COBRA HA VLPs.

Three weeks after final vaccination, ferrets are challenged intranasally with a highly pathogenic H1N1 virus in a volume of 1 ml. After infection, ferrets are monitored daily for weight loss, disease signs and death for 14 days after infection. Individual body weights, sickness scores, and death are recorded for each group on each day after inoculation. Nasal washes are performed by instilling 3 ml of PBS into the nares of anesthetized ferrets each day for 7 days after inoculation. Washes are collected and stored at −80° C. until use.

Primate Immunizations

Cynomolgus macaques (*Macaca fascicularis*, male, 3-5 years old) can be purchased from Harlan Sprague Dawley (Indianapolis, Ind., USA). Macaques are vaccinated with purified COBRA HA VLPs (15 μg), based upon HA content from a densitometry assay, via intramuscular injection at week 0 and then boosted with the same dose at weeks 3 and 6. Vaccines are formulated with alum adjuvant (Imject Alum, Pierce Biotechnology; Rockford, Ill., USA) immediately prior to use. Twenty-one days after each vaccination, blood is collected from anesthetized macaques via the femoral vein and transferred to a serum separator tube. Tubes are allowed to activate clotting followed by centrifugation and sera is removed and frozen at −80±5° C. End point IgG titers and HAI serum antibody titer for each vaccine group is determined at week 5 using representative reassortant viruses or COBRA HA VLPs.

Three weeks after final vaccination, macaques are challenged by intranasal, intratracheal, and orbital inoculation with a highly pathogenic H1N1 virus in a volume of 1 ml. After infection, macaques are monitored daily for weight loss, disease signs and death for 5 days after infection. Individual body weights, sickness scores and death are recorded for each group on each day after inoculation.

Example 3: Analysis of COBRA H1N1 Method 1 HA

This example describes the finding that inoculation of mice with COBRA H1N1 influenza VLPs induces significant HAI serum antibody titers, and further shows that translation of COBRA H1N1 HA in vitro results in expression of the protein at the expected molecular weight.

HAI Serum Antibody Titers

Figure 6:
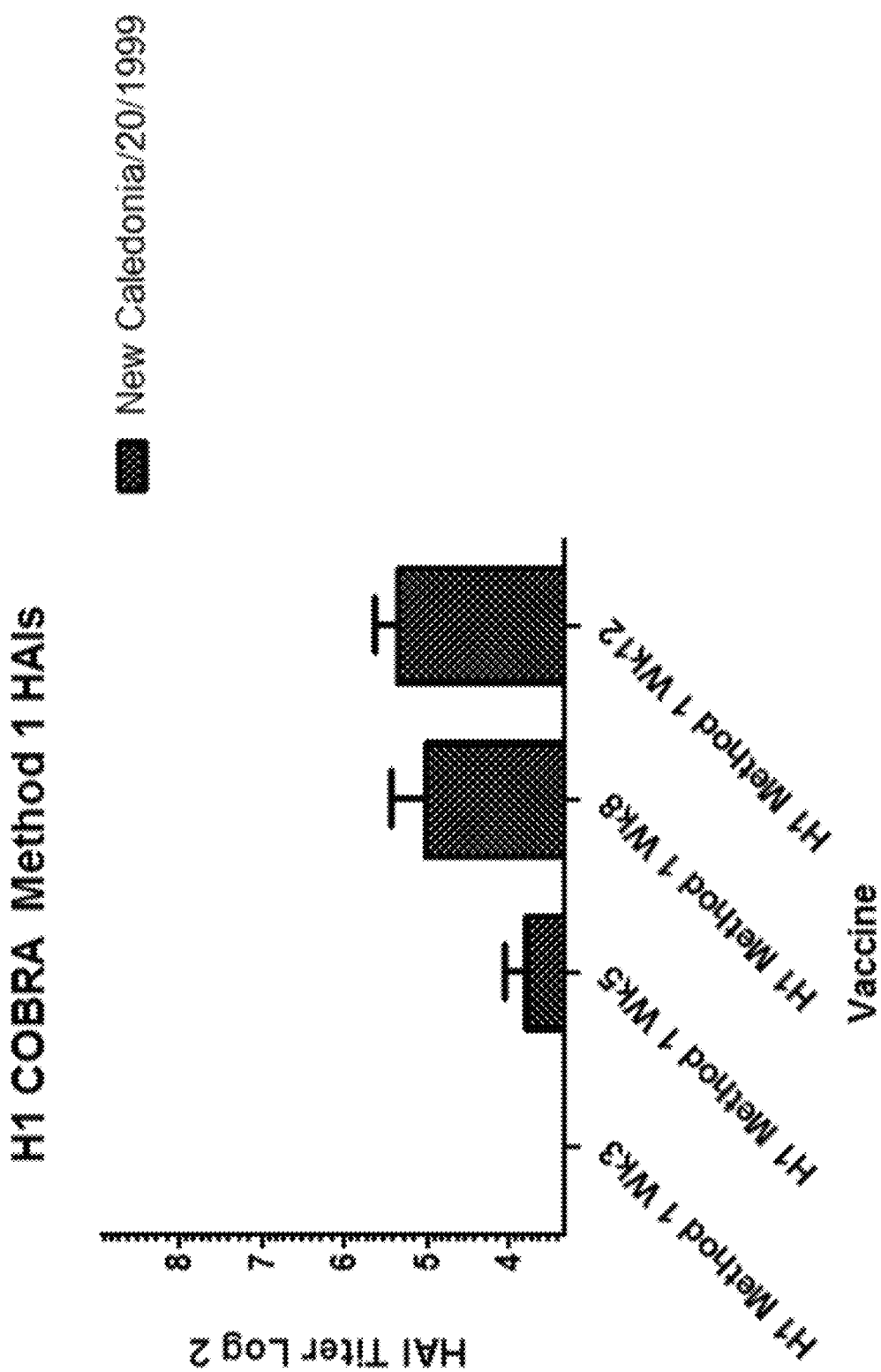
FIG. 6 is a graph showing hemagglutination-inhibition (HAI) serum antibody titers induced by COBRA H1N1 infection of mice. HAI serum antibody titers were determined in mice infected with COBRA H1N1 influenza VLPs (COBRA Method 1). Antisera were tested against the seasonal H1N1 influenza virus, A/New Caledonia/20/1999. The results are represented as the log 2 transformed geometric mean titer (±S.E.M.) from antisera collected at weeks 3, 5, 8 and 12 post-infection.

To evaluate whether influenza virus containing COBRA Method 1 H1N1 HA is capable of eliciting an antibody response in infected animals, VLPs comprising the COBRA Method 1 HA (SEQ ID NO: 1) were generated as described in Example 2. Mice were inoculated with the VLPs and serum was collected at weeks 3, 5, 8 and 12 post-infection for determination of HAI serum antibody titers. Antisera were tested against the seasonal H1N1 influenza virus, A/New Caledonia/20/1999. As shown in FIG. 6, HAI titers were detected starting at 5 weeks post-infection and increased at weeks 8 and 12.

Expression of COBRA HA In Vitro

Figure 7:
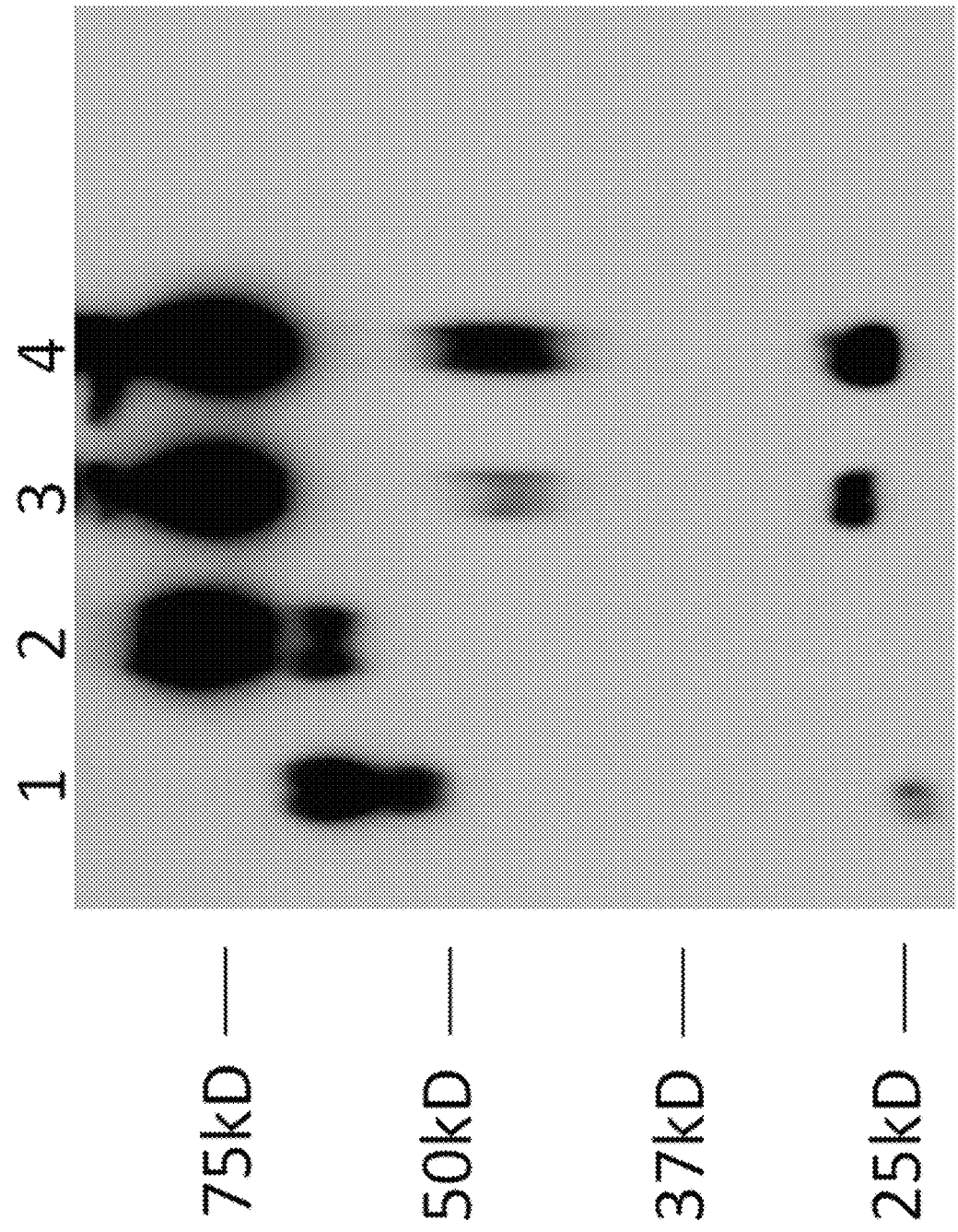
FIG. 7 is Western blot showing expression of COBRA HA protein (Method 1 consensus sequence). COBRA H1N1 HA was translated in vitro and the cell culture lysates were analyzed by SDS-PAGE and Western blot. Lane 1, A/New Caledonia/20/1999 virus; Lane 2, H1N1 COBRA secreted HA; Lane 3, H1N1 COBRA 5 μg VLP; Lane 4, COBRA 10 μg VLP. The COBRA HA (lane 2) migrates at its expected molecular weight confirming expression of the synthetic protein.

As described in Example 2, the COBRA HA Method 1 amino acid sequence was reverse translated and optimized for expression in mammalian cells. The optimized nucleic acid sequence (SEQ ID NO: 13) encoding COBRA HA was inserted into the pTR600 expression vector. To assess whether COBRA H1N1 HA is properly expressed in vitro, cells were transfected with the pTR600 expression vector encoding COBRA H1N1 HA. Cell culture lysates were analyzed by SDS-PAGE, followed by Western blot for detection of influenza HA. As shown in FIG. 7, COBRA HA migrated to its expected molecular weight, confirming expression of the synthetic protein in vitro.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

SEQUENCE LISTING

```
<160> NUMBER OF SEQ ID NOS: 13

<210> SEQ ID NO 1
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 1

Met Lys Ala Lys Leu Leu Val Leu Leu Cys Ala Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Asn Cys Ser Ile Ala Gly Trp Ile Leu Gly
65                  70                  75                  80

Asn Pro Glu Cys Glu Ser Leu Phe Ser Lys Glu Ser Trp Ser Tyr Ile
                85                  90                  95

Val Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Thr Ala Ser Cys Ser His Asn Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
        195                 200                 205

Tyr His Thr Glu Asn Ala Tyr Val Ser Val Val Ser Ser His Tyr Ser
    210                 215                 220

Arg Arg Phe Thr Pro Glu Ile Ala Lys Arg Pro Lys Val Arg Asp Gln
225                 230                 235                 240
```

-continued

Glu Gly Arg Ile Asn Tyr Tyr Trp Thr Leu Leu Pro Gly Asp Thr
            245                 250                 255

Ile Ile Phe Glu Ala Asn Gly Asn Leu Ile Ala Pro Trp Tyr Ala Phe
        260                 265                 270

Ala Leu Ser Arg Gly Phe Gly Ser Gly Ile Ile Thr Ser Asn Ala Ser
    275                 280                 285

Met Asp Glu Cys Asp Ala Lys Cys Gln Thr Pro Gln Gly Ala Ile Asn
290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 2
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 2

Met Lys Ala Lys Leu Leu Val Leu Leu Cys Ala Leu Thr Ala Thr Asp
1               5                   10                  15

Ala Asp Thr Ile Cys Ile Gly Tyr His Ala Asn Asn Ser Thr Asp Thr
            20                  25                  30

-continued

```
Val Asp Thr Val Leu Glu Lys Asn Val Thr Val His Ser Val Asn
        35                  40                  45

Leu Leu Glu Asp Ser His Asn Gly Lys Leu Cys Arg Leu Lys Gly Ile
 50                  55                  60

Ala Pro Leu Gln Leu Gly Asn Cys Ser Ile Ala Gly Trp Ile Leu Gly
 65                  70                  75                  80

Asn Pro Glu Cys Glu Ser Leu Phe Ser Lys Lys Ser Trp Ser Tyr Ile
                 85                  90                  95

Ala Glu Thr Pro Asn Ser Glu Asn Gly Thr Cys Tyr Pro Gly Tyr Phe
                100                 105                 110

Ala Asp Tyr Glu Glu Leu Arg Glu Gln Leu Ser Ser Val Ser Ser Phe
                115                 120                 125

Glu Arg Phe Glu Ile Phe Pro Lys Glu Ser Ser Trp Pro Asn His Thr
                130                 135                 140

Val Thr Lys Gly Val Thr Ala Ala Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
                180                 185                 190

Leu Trp Gly Val His His Pro Ser Asn Ile Gly Asp Gln Arg Ala Ile
                195                 200                 205

Tyr His Thr Glu Asn Ala Tyr Val Ser Val Val Ser Ser His Tyr Asn
                210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
                260                 265                 270

Ala Leu Ser Arg Gly Phe Gly Ser Gly Ile Ile Thr Ser Asn Ala Ser
                275                 280                 285

Met Asp Glu Cys Asp Ala Lys Cys Gln Thr Pro Gln Gly Ala Ile Asn
                290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
                355                 360                 365

His His Gln Asn Glu Gln Gly Ser Gly Tyr Ala Ala Asp Gln Lys Ser
                370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
                435                 440                 445
```

```
Glu Arg Thr Leu Asp Phe His Asp Ser Asn Val Lys Asn Leu Tyr Glu
    450                 455                 460
Lys Val Lys Ser Gln Leu Lys Asn Asn Ala Lys Glu Ile Gly Asn Gly
465                 470                 475                 480
Cys Phe Glu Phe Tyr His Lys Cys Asn Asn Glu Cys Met Glu Ser Val
                485                 490                 495
Lys Asn Gly Thr Tyr Asp Tyr Pro Lys Tyr Ser Glu Glu Ser Lys Leu
            500                 505                 510
Asn Arg Glu Lys Ile Asp Gly Val Lys Leu Glu Ser Met Gly Val Tyr
        515                 520                 525
Gln Ile Leu Ala Ile Tyr Ser Thr Val Ala Ser Ser Leu Val Leu Leu
    530                 535                 540
Val Ser Leu Gly Ala Ile Ser Phe Trp Met Cys Ser Asn Gly Ser Leu
545                 550                 555                 560
Gln Cys Arg Ile Cys Ile
                565

<210> SEQ ID NO 3
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 3

Met Lys Ala Lys Leu Leu Val Leu Leu Cys Ala Phe Thr Ala Thr Tyr
1               5                   10                  15
Ala Asp Thr Ile Cys Ile Gly Tyr His Ala Asn Asn Ser Thr Asp Thr
                20                  25                  30
Val Asp Thr Val Leu Glu Lys Asn Val Thr Val Thr His Ser Val Asn
            35                  40                  45
Leu Leu Glu Asp Ser His Asn Gly Lys Leu Cys Arg Leu Lys Gly Ile
        50                  55                  60
Ala Pro Leu Gln Leu Gly Asn Cys Ser Val Ala Gly Trp Ile Leu Gly
65                  70                  75                  80
Asn Pro Glu Cys Glu Ser Leu Ile Ser Lys Glu Ser Trp Ser Tyr Ile
                85                  90                  95
Val Glu Thr Pro Asn Pro Glu Asn Gly Thr Cys Tyr Pro Gly Tyr Phe
                100                 105                 110
Ala Asp Tyr Glu Glu Leu Arg Glu Gln Leu Ser Ser Val Ser Ser Phe
            115                 120                 125
Glu Arg Phe Glu Ile Phe Pro Lys Glu Ser Ser Trp Pro Asn His Thr
        130                 135                 140
Val Thr Lys Gly Val Thr Ala Ser Cys Ser His Asn Gly Lys Ser Ser
145                 150                 155                 160
Phe Tyr Arg Asn Leu Leu Trp Leu Thr Glu Lys Asn Gly Leu Tyr Pro
                165                 170                 175
Asn Leu Ser Lys Ser Tyr Val Asn Asn Lys Glu Lys Glu Val Leu Val
                180                 185                 190
Leu Trp Gly Val His His Pro Ser Asn Ile Gly Asp Gln Arg Ala Leu
            195                 200                 205
Tyr His Thr Glu Asn Ala Tyr Val Ser Val Ser Ser His Tyr Ser
        210                 215                 220
Arg Arg Phe Thr Pro Glu Ile Ala Lys Arg Pro Lys Val Arg Asp Gln
225                 230                 235                 240
```

```
Glu Gly Arg Ile Asn Tyr Tyr Trp Thr Leu Glu Pro Gly Asp Thr
            245                 250                 255

Ile Ile Phe Glu Ala Asn Gly Asn Leu Ile Ala Pro Trp Tyr Ala Phe
        260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
        370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
            565
```

<210> SEQ ID NO 4
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 4

```
Met Lys Ala Lys Leu Leu Val Leu Leu Cys Ala Leu Thr Ala Thr Asp
1               5                   10                  15

Ala Asp Thr Ile Cys Ile Gly Tyr His Ala Asn Asn Ser Thr Asp Thr
            20                  25                  30
```

-continued

```
Val Asp Thr Val Leu Glu Lys Asn Val Thr Val Thr His Ser Val Asn
         35                  40                  45

Leu Leu Glu Asp Ser His Asn Gly Lys Leu Cys Arg Leu Lys Gly Ile
 50                  55                  60

Ala Pro Leu Gln Leu Gly Lys Cys Ser Ile Ala Gly Trp Ile Leu Gly
 65                  70                  75                  80

Asn Pro Glu Cys Glu Ser Leu Leu Ser Lys Ser Trp Ser Tyr Ile
                     85                  90                  95

Ala Glu Thr Pro Asn Ser Glu Asn Gly Thr Cys Tyr Pro Gly Tyr Phe
             100                 105                 110

Ala Asp Tyr Glu Glu Leu Arg Glu Gln Leu Ser Ser Val Ser Ser Phe
             115                 120                 125

Glu Arg Phe Glu Ile Phe Pro Lys Glu Ser Ser Trp Pro Asn His Asn
130                 135                 140

Val Thr Lys Gly Val Thr Ala Ser Cys Ser His Lys Gly Lys Ser Ser
145                 150                 155                 160

Phe Tyr Arg Asn Leu Leu Trp Leu Thr Glu Lys Asn Gly Ser Tyr Pro
                 165                 170                 175

Asn Leu Ser Lys Ser Tyr Val Asn Asn Lys Glu Lys Glu Val Leu Val
             180                 185                 190

Leu Trp Gly Val His His Pro Ser Asn Ile Gly Asp Gln Arg Thr Ile
         195                 200                 205

Tyr Arg Thr Glu Asn Ala Tyr Val Ser Val Val Ser Ser Asn Tyr Asn
     210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                 245                 250                 255

Ile Ile Phe Glu Ala Asn Gly Asn Leu Ile Ala Pro Trp Tyr Ala Phe
             260                 265                 270

Ala Leu Ser Arg Gly Phe Gly Ser Gly Ile Ile Thr Ser Asn Ala Ser
         275                 280                 285

Met Asp Glu Cys Asp Thr Lys Cys Gln Thr Pro Gln Gly Ala Ile Asn
290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                 325                 330                 335

Asn Ile Pro Ser Ile Gln Ser Arg Gly Leu Phe Gly Ala Ile Ala Gly
             340                 345                 350

Phe Ile Glu Gly Gly Trp Thr Gly Met Ile Asp Gly Trp Tyr Gly Tyr
         355                 360                 365

His His Gln Asn Glu Gln Gly Ser Gly Tyr Ala Ala Asp Gln Lys Ser
     370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                 405                 410                 415

Leu Glu Lys Arg Met Glu Asn Leu Asn Lys Lys Val Asp Asp Gly Phe
             420                 425                 430

Leu Asp Ile Trp Thr Tyr Asn Ala Glu Leu Leu Val Leu Leu Glu Asn
         435                 440                 445

Glu Arg Thr Leu Asp Phe His Asp Ser Asn Val Lys Asn Leu Tyr Glu
```

```
                450             455              460
Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Ser Lys Leu
                500                 505                 510

Asn Arg Glu Lys Ile Asp Gly Val Lys Leu Glu Ser Met Gly Val Tyr
            515                 520                 525

Gln Ile Leu Ala Ile Tyr Ser Thr Val Ala Ser Ser Leu Val Leu Leu
            530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 5
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 5

Met Lys Ala Lys Leu Leu Val Leu Leu Cys Thr Phe Thr Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Asn Cys Ser Ile Ala Gly Trp Ile Leu Gly
65                  70                  75                  80

Asn Pro Glu Cys Glu Ser Leu Leu Ser Lys Lys Ser Trp Ser Tyr Ile
                85                  90                  95

Val Glu Thr Pro Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Thr Ala Ala Cys Ser His Ala Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Gly Lys Glu Val Leu Val
            180                 185                 190

Leu Trp Gly Val His His Pro Ser Asn Ile Gly Asp Gln Gln Ala Leu
        195                 200                 205

Tyr Gln Thr Glu Asn Ala Tyr Val Ser Val Val Ser Ser His Tyr Asn
    210                 215                 220

Arg Lys Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
```

```
                245                 250                 255
Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met His Glu Cys Asp Thr Lys Cys Gln Thr Pro Gln Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 6
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 6

Met Lys Ala Lys Leu Leu Val Leu Leu Cys Ala Phe Thr Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
```

```
            35                  40                  45
Leu Leu Glu Asp Ser His Asn Gly Lys Leu Cys Lys Leu Lys Gly Ile
 50                  55                  60

Ala Pro Leu Gln Leu Gly Lys Cys Ser Ile Ala Gly Trp Ile Leu Gly
 65                  70                  75                  80

Asn Pro Glu Cys Glu Ser Leu Leu Ser Lys Ser Trp Ser Tyr Ile
                     85                  90                  95

Val Glu Thr Pro Asn Ser Glu Asn Gly Thr Cys Tyr Pro Gly Asp Phe
                100                 105                 110

Ala Asp Tyr Glu Glu Leu Arg Glu Gln Leu Ser Ser Val Ser Ser Phe
                115                 120                 125

Glu Arg Phe Glu Ile Phe Pro Lys Glu Ser Ser Trp Pro Asn His Thr
        130                 135                 140

Val Thr Lys Gly Val Thr Ala Ala Cys Ser His Ala Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
                180                 185                 190

Leu Trp Gly Val His His Pro Ser Asn Ile Gly Asp Gln Arg Ala Leu
        195                 200                 205

Tyr His Thr Glu Asn Ala Tyr Val Ser Val Val Ser Ser His Tyr Asn
210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
                260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
        370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
450                 455                 460
```

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
            485                 490                 495

Lys Asn Gly Thr Tyr Asp Tyr Pro Lys Tyr Ser Glu Glu Ser Lys Leu
        500                 505                 510

Asn Arg Glu Lys Ile Asp Gly Val Lys Leu Glu Ser Met Gly Val Tyr
            515                 520                 525

Gln Ile Leu Ala Ile Tyr Ser Thr Val Ala Ser Ser Leu Val Leu Leu
        530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 7
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 7

Met Lys Ala Lys Leu Leu Val Leu Leu Cys Thr Phe Thr Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Asn Cys Ala Ile Ala Gly Trp Ile Leu Gly
65                  70                  75                  80

Asn Pro Glu Cys Glu Ser Leu Leu Ser Lys Ser Trp Ser Tyr Ile
                85                  90                  95

Val Glu Thr Pro Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Ala
    130                 135                 140

Val Thr Lys Gly Val Thr Ala Ala Cys Ser His Ala Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ala Lys Ser Tyr Val Asn Asn Lys Gly Lys Glu Val Leu Val
            180                 185                 190

Leu Trp Gly Val His His Pro Ser Asn Ile Gly Asp Gln Gln Ala Leu
        195                 200                 205

Tyr Gln Thr Glu Asn Ala Tyr Val Ser Val Val Ser Ser His Tyr Asn
    210                 215                 220

Arg Lys Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
                260                 265                 270

Ala Leu Ser Arg Gly Phe Gly Ser Gly Ile Ile Thr Ser Asn Ala Ala
            275                 280                 285

Met His Glu Cys Asp Thr Lys Cys Gln Thr Pro Gln Gly Ala Ile Asn
        290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 8
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 8

Met Lys Ala Arg Leu Leu Val Leu Leu Cys Ala Leu Ala Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

```
Leu Leu Glu Asp Ser His Asn Gly Lys Leu Cys Arg Leu Lys Gly Ile
        50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Asn Arg Ser Trp Ser Tyr Ile
                85                  90                  95

Val Glu Thr Pro Asn Ser Glu Asn Gly Thr Cys Tyr Pro Gly Asp Phe
                100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Lys His Asn
        130                 135                 140

Thr Thr Lys Gly Val Thr Ala Ala Cys Ser His Ala Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Asn Ser Tyr Val Asn Asn Lys Gly Lys Glu Val Leu Val
                180                 185                 190

Leu Trp Gly Val His His Pro Ser Asn Ile Asp Asp Gln Gln Thr Leu
            195                 200                 205

Tyr Gln Lys Glu Asn Ala Tyr Val Ser Val Val Ser Ser Asn Tyr Asn
        210                 215                 220

Arg Arg Phe Thr Pro Glu Ile Ala Glu Arg Pro Lys Val Arg Gly Gln
225                 230                 235                 240

Ala Gly Arg Met Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met His Glu Cys Asp Thr Lys Cys Gln Thr Pro Gln Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
450                 455                 460
```

```
Lys Val Lys Ser Gln Leu Arg Asn Asn Ala Lys Glu Ile Gly Asn Gly
465                 470                 475                 480

Cys Phe Glu Phe Tyr His Lys Cys Asp Asn Glu Cys Met Glu Ser Val
            485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
            515                 520                 525

Gln Ile Leu Ala Ile Tyr Ser Thr Val Ala Ser Ser Leu Val Leu Leu
            530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 9
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 9

```
Met Lys Ala Lys Leu Leu Val Leu Leu Cys Ala Phe Thr Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
        50                  55                  60

Ala Pro Leu Gln Leu Gly Asn Cys Ser Ile Ala Gly Trp Ile Leu Gly
65                  70                  75                  80

Asn Pro Glu Cys Glu Ser Leu Phe Ser Lys Ser Trp Ser Tyr Ile
            85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
130                 135                 140

Val Thr Lys Gly Val Thr Ala Ser Cys Ser His Lys Gly Lys Ser Ser
145                 150                 155                 160

Phe Tyr Arg Asn Leu Leu Trp Leu Thr Glu Lys Asn Gly Ser Tyr Pro
            165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
            195                 200                 205

Tyr His Thr Glu Asn Ala Tyr Val Ser Val Val Ser Ser His Tyr Asn
            210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
            245                 250                 255
```

-continued

```
Ile Ile Phe Glu Ala Asn Gly Asn Leu Ile Ala Pro Trp Tyr Ala Phe
                260                 265                 270

Ala Leu Ser Arg Gly Phe Gly Ser Gly Ile Ile Thr Ser Asn Ala Ser
            275                 280                 285

Met Asp Glu Cys Asp Ala Lys Cys Gln Thr Pro Gln Gly Ala Ile Asn
        290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

```
<210> SEQ ID NO 10
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 10

Met Lys Ala Ile Leu Val Leu Cys Thr Phe Ala Ala Thr Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45
```

-continued

```
Leu Leu Glu Asp Lys His Asn Gly Lys Leu Cys Lys Leu Lys Gly Ile
 50                  55                  60

Ala Pro Leu His Leu Gly Lys Cys Asn Ile Ala Gly Trp Leu Leu Gly
 65                  70                  75                  80

Asn Pro Glu Cys Glu Leu Leu Leu Thr Ala Ser Ser Trp Ser Tyr Ile
                 85                  90                  95

Val Glu Thr Ser Asn Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Glu
130                 135                 140

Thr Asn Lys Gly Val Thr Ala Ala Cys Pro Tyr Ala Gly Ala Ser Ser
145                 150                 155                 160

Phe Tyr Arg Asn Leu Ile Trp Leu Val Lys Lys Gly Asn Ser Tyr Pro
                165                 170                 175

Lys Leu Ser Lys Ser Tyr Val Asn Asn Lys Gly Lys Glu Val Leu Val
            180                 185                 190

Leu Trp Gly Ile His His Pro Pro Thr Ser Thr Asp Gln Gln Ser Leu
        195                 200                 205

Tyr Gln Asn Ala Asp Ala Tyr Val Phe Val Gly Ser Ser Lys Tyr Asn
210                 215                 220

Arg Lys Phe Lys Pro Glu Ile Ala Ala Arg Pro Lys Val Arg Asp Gln
225                 230                 235                 240

Ala Gly Arg Met Asn Tyr Tyr Trp Thr Leu Ile Glu Pro Gly Asp Thr
                245                 250                 255

Ile Thr Phe Glu Ala Thr Gly Asn Leu Val Val Pro Arg Tyr Ala Phe
            260                 265                 270

Ala Met Asn Arg Gly Ser Gly Ser Gly Ile Ile Ile Ser Asp Ala Pro
        275                 280                 285

Val His Asp Cys Asn Thr Lys Cys Gln Thr Pro Lys Gly Ala Ile Asn
290                 295                 300

Thr Ser Leu Pro Phe Gln Asn Ile His Pro Val Thr Ile Gly Glu Cys
305                 310                 315                 320

Pro Lys Tyr Val Lys Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
450                 455                 460

Lys Val Arg Ser Gln Leu Lys Asn Asn Ala Lys Glu Ile Gly Asn Gly
```

```
            465                 470                 475                 480
Cys Phe Glu Phe Tyr His Lys Cys Asp Asp Thr Cys Met Glu Ser Val
                485                 490                 495

Lys Asn Gly Thr Tyr Asp Tyr Pro Lys Tyr Ser Glu Glu Ser Lys Leu
                500                 505                 510

Asn Arg Glu Glu Ile Asp Gly Val Lys Leu Glu Ser Thr Arg Ile Tyr
                515                 520                 525

Gln Ile Leu Ala Ile Tyr Ser Thr Val Ala Ser Ser Leu Val Leu Leu
                530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 11
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 11

Met Lys Ala Ile Leu Val Leu Leu Cys Thr Phe Thr Ala Ala Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
                35                  40                  45

Leu Leu Glu Asp Arg His Asn Gly Lys Leu Cys Lys Leu Gly Gly Ile
                50                  55                  60

Ala Pro Leu His Leu Gly Lys Cys Asn Ile Ala Gly Trp Leu Leu Gly
65                  70                  75                  80

Asn Pro Glu Cys Glu Leu Leu Leu Thr Ala Ser Ser Trp Ser Tyr Ile
                85                  90                  95

Val Glu Thr Ser Asn Ser Asp Asn Gly Thr Cys Tyr Pro Gly Asp Phe
                100                 105                 110

Ile Asn Tyr Glu Glu Leu Arg Glu Gln Leu Ser Ser Val Ser Ser Phe
                115                 120                 125

Glu Arg Phe Glu Ile Phe Pro Lys Ala Ser Ser Trp Pro Asn His Glu
                130                 135                 140

Thr Asn Arg Gly Val Thr Ala Ala Cys Pro Tyr Ala Gly Ala Asn Ser
145                 150                 155                 160

Phe Tyr Arg Asn Leu Ile Trp Leu Val Lys Lys Gly Asn Ser Tyr Pro
                165                 170                 175

Lys Leu Ser Lys Ser Tyr Val Asn Asn Lys Gly Lys Glu Val Leu Val
                180                 185                 190

Leu Trp Gly Ile His His Pro Pro Thr Ser Thr Asp Gln Gln Ser Leu
                195                 200                 205

Tyr Gln Asn Ala Asp Ala Tyr Val Phe Val Gly Ser Ser Lys Tyr Asn
                210                 215                 220

Arg Lys Phe Lys Pro Glu Ile Ala Ala Arg Pro Lys Val Arg Gly Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Thr Gly Asn Leu Val Val Pro Arg Tyr Ala Phe
```

-continued

```
                260                 265                 270
Ala Met Asn Arg Gly Ser Gly Ser Gly Ile Ile Ile Ser Asp Ala Pro
            275                 280                 285

Val His Asp Cys Asn Thr Lys Cys Gln Thr Pro Lys Gly Ala Ile Asn
        290                 295                 300

Thr Ser Leu Pro Phe Gln Asn Ile His Pro Val Thr Ile Gly Glu Cys
305                 310                 315                 320

Pro Lys Tyr Val Lys Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Val Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Arg Ser Gln Leu Arg Asn Asn Ala Lys Glu Ile Gly Asn Gly
465                 470                 475                 480

Cys Phe Glu Phe Tyr His Lys Cys Asp Asp Thr Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 12
<211> LENGTH: 566
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:

```
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(74)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (88)..(91)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (102)..(103)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (113)..(114)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (144)..(147)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (154)..(156)
<223> OTHER INFORMATION: Xaa can be any naturally occurring amino acid
```

```
<220> FEATURE:
<221> NAME/KEY: misc_feature
<222> LOCATION: (158)..(159)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (169)..(170)
<223> OTHER INFORMATION: Xaa can be any naturally occurring amino acid
<220> FEATURE:
<221> NAME/KEY: misc_feature
<222> LOCATION: (172)..(174)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (179)..(180)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (196)..(196)
<223> OTHER INFORMATION: Xaa can be any naturally occurring amino acid
<220> FEATURE:
<221> NAME/KEY: misc_feature
<222> LOCATION: (200)..(203)
<223> OTHER INFORMATION: Xaa can be any naturally occurring amino acid
<220> FEATURE:
<221> NAME/KEY: misc_feature
<222> LOCATION: (206)..(208)
<223> OTHER INFORMATION: Xaa can be any naturally occurring amino acid
<220> FEATURE:
<221> NAME/KEY: misc_feature
<222> LOCATION: (210)..(213)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (233)..(233)
<223> OTHER INFORMATION: Xaa can be any naturally occurring amino acid
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (241)..(241)
```

```
<223> OTHER INFORMATION: Xaa can be any naturally occurring amino acid
<220> FEATURE:
<221> NAME/KEY: misc_feature
<222> LOCATION: (244)..(244)
<223> OTHER INFORMATION: Xaa can be any naturally occurring amino acid
<220> FEATURE:
<221> NAME/KEY: misc_feature
<222> LOCATION: (251)..(251)
<223> OTHER INFORMATION: Xaa can be any naturally occurring amino acid
<220> FEATURE:
<221> NAME/KEY: misc_feature
<222> LOCATION: (258)..(258)
<223> OTHER INFORMATION: Xaa can be any naturally occurring amino acid
<220> FEATURE:
<221> NAME/KEY: misc_feature
<222> LOCATION: (262)..(262)
<223> OTHER INFORMATION: Xaa can be any naturally occurring amino acid
<220> FEATURE:
<221> NAME/KEY: misc_feature
<222> LOCATION: (266)..(267)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (274)..(275)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (284)..(284)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (288)..(291)
<223> OTHER INFORMATION: Xaa can be any naturally occurring amino acid
<220> FEATURE:
<221> NAME/KEY: misc_feature
<222> LOCATION: (293)..(294)
<223> OTHER INFORMATION: Xaa can be any naturally occurring amino acid
<220> FEATURE:
<221> NAME/KEY: misc_feature
<222> LOCATION: (300)..(300)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (312)..(312)
<223> OTHER INFORMATION: Xaa can be any naturally occurring amino acid
<220> FEATURE:
<221> NAME/KEY: misc_feature
<222> LOCATION: (325)..(325)
<223> OTHER INFORMATION: Xaa can be any naturally occurring amino acid
<220> FEATURE:
<221> NAME/KEY: misc_feature
<222> LOCATION: (332)..(332)
<223> OTHER INFORMATION: Xaa can be any naturally occurring amino acid
<220> FEATURE:
<221> NAME/KEY: misc_feature
<222> LOCATION: (390)..(390)
<223> OTHER INFORMATION: Xaa can be any naturally occurring amino acid
<220> FEATURE:
<221> NAME/KEY: misc_feature
<222> LOCATION: (416)..(416)
<223> OTHER INFORMATION: Xaa can be any naturally occurring amino acid
<220> FEATURE:
<221> NAME/KEY: misc_feature
```

```
<222> LOCATION: (419)..(419)
<223> OTHER INFORMATION: Xaa can be any naturally occurring amino acid
<220> FEATURE:
<221> NAME/KEY: misc_feature
<222> LOCATION: (421)..(421)
<223> OTHER INFORMATION: Xaa can be any naturally occurring amino acid
<220> FEATURE:
<221> NAME/KEY: misc_feature
<222> LOCATION: (435)..(435)
<223> OTHER INFORMATION: Xaa can be any naturally occurring amino acid
<220> FEATURE:
<221> NAME/KEY: misc_feature
<222> LOCATION: (467)..(467)
<223> OTHER INFORMATION: Xaa can be any naturally occurring amino acid
<220> FEATURE:
<221> NAME/KEY: misc_feature
<222> LOCATION: (471)..(471)
<223> OTHER INFORMATION: Xaa can be any naturally occurring amino acid
<220> FEATURE:
<221> NAME/KEY: misc_feature
<222> LOCATION: (489)..(491)
<223> OTHER INFORMATION: Xaa can be any naturally occurring amino acid
<220> FEATURE:
<221> NAME/KEY: misc_feature
<222> LOCATION: (516)..(516)
<223> OTHER INFORMATION: Xaa can be any naturally occurring amino acid
<220> FEATURE:
<221> NAME/KEY: misc_feature
<222> LOCATION: (525)..(527)
<223> OTHER INFORMATION: Xaa can be any naturally occurring amino acid

<400> SEQUENCE: 12

Met Lys Ala Xaa Leu Leu Val Leu Leu Cys Xaa Xaa Ala Xaa Xaa
1               5                   10                  15

Ala Asp Thr Xaa Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Xaa His Asn Gly Lys Leu Cys Xaa Leu Xaa Gly Ile
    50                  55                  60

Ala Pro Leu Xaa Leu Gly Xaa Cys Xaa Xaa Ala Gly Trp Xaa Leu Gly
65                  70                  75                  80

Asn Pro Glu Cys Glu Xaa Leu Xaa Xaa Xaa Xaa Ser Trp Ser Tyr Ile
                85                  90                  95

Xaa Glu Thr Xaa Asn Xaa Xaa Asn Gly Thr Cys Tyr Pro Gly Xaa Phe
            100                 105                 110

Xaa Xaa Tyr Glu Glu Leu Arg Glu Gln Leu Ser Ser Val Ser Ser Phe
        115                 120                 125

Glu Arg Phe Glu Ile Phe Pro Lys Xaa Ser Ser Trp Pro Xaa His Xaa
130                 135                 140

Xaa Xaa Xaa Gly Val Thr Ala Xaa Cys Xaa Xaa Xaa Gly Xaa Xaa Ser
145                 150                 155                 160

Phe Tyr Arg Asn Leu Xaa Trp Leu Xaa Xaa Lys Xaa Xaa Xaa Tyr Pro
                165                 170                 175

Xaa Leu Xaa Xaa Ser Tyr Val Asn Asn Lys Xaa Lys Glu Val Leu Val
            180                 185                 190

Leu Trp Gly Xaa His His Pro Xaa Xaa Xaa Asp Gln Xaa Xaa Xaa
        195                 200                 205

Tyr Xaa Xaa Xaa Xaa Ala Tyr Val Xaa Val Xaa Ser Ser Xaa Tyr Xaa
            210                 215                 220

Arg Xaa Phe Xaa Pro Glu Ile Ala Xaa Arg Pro Lys Val Arg Xaa Gln
225                 230                 235                 240

Xaa Gly Arg Xaa Asn Tyr Tyr Trp Thr Leu Xaa Glu Pro Gly Asp Thr
```

```
            245                 250                 255
Ile Xaa Phe Glu Ala Xaa Gly Asn Leu Xaa Xaa Pro Xaa Tyr Ala Phe
            260                 265                 270

Ala Xaa Xaa Arg Gly Xaa Gly Ser Gly Ile Ile Xaa Ser Xaa Ala Xaa
        275                 280                 285

Xaa Xaa Xaa Cys Xaa Xaa Lys Cys Gln Thr Pro Xaa Gly Ala Ile Asn
    290                 295                 300

Xaa Ser Leu Pro Phe Gln Asn Xaa His Pro Val Thr Ile Gly Glu Cys
305                 310                 315                 320

Pro Lys Tyr Val Xaa Ser Thr Lys Leu Arg Met Xaa Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
        370                 375                 380

Thr Gln Asn Ala Ile Xaa Gly Ile Thr Asn Lys Val Asn Ser Val Ile
385                 390                 395                 400

Glu Lys Met Asn Thr Gln Phe Thr Ala Val Gly Lys Glu Phe Asn Xaa
                405                 410                 415

Leu Glu Xaa Arg Xaa Glu Asn Leu Asn Lys Lys Val Asp Asp Gly Phe
            420                 425                 430

Leu Asp Xaa Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Xaa Ser Gln Leu Xaa Asn Asn Ala Lys Glu Ile Gly Asn Gly
465                 470                 475                 480

Cys Phe Glu Phe Tyr His Lys Cys Xaa Xaa Xaa Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Xaa Ile Asp Gly Val Lys Leu Glu Ser Xaa Xaa Xaa Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 13
<211> LENGTH: 1719
<212> TYPE: DNA
<213> ORGANISM: Artificial Sequence
<220> FEATURE:
<223> OTHER INFORMATION: Synthetic construct

<400> SEQUENCE: 13
aagcttatga aggccaagct gctggtgctg ctgtgcgcct tcacagccac ctacgccgac      60
accatctgca tcggctacca cgccaacaac agcaccgaca ccgtggatac cgtgctggaa     120
aagaacgtga ccgtgaccca cagcgtgaac ctgctggaag atagccacaa cggcaagctg     180
tgccggctga agggaatcgc ccctctgcag ctgggcaact gctctatcgc cggctggatt     240
```

```
ctgggcaacc ccgagtgcga gagcctgttc agcaaagagt cctggtccta catcgtggaa      300
acccccaaca gcgagaacgg cacctgttac cccggctact tcgccgacta cgaggaactg      360
cgggaacagc tgagcagcgt gtccagcttc gagagattcg agattttccc caaagagagc      420
agctggccca accacaccgt gaccaaaggc gtgaccgcct cctgctccca caatggcaag      480
agcagcttct acagaaacct gctgtggctg accgagaaga acggcagcta ccccaacctg      540
agcaagagct acgtgaacaa caagaaaaaa gaggtgctgg tgctgtgggg cgtgcaccac      600
cctagcaaca tcggcgacca gcgggccatc taccacaccg agaatgccta cgtgtccgtg      660
gtgtccagcc actacagcag acggttcacc cccgagatcg ccaagaggcc caaagtgcgg      720
gaccaggaag gccggatcaa ctactactgg acactgctgg aacccggcga taccatcatc      780
ttcgaggcca acggcaacct gatcgcccct tggtacgcct tcgccctgag cagaggcttt      840
ggcagcggca tcatcaccag caacgccagc atggacgagt gcgacgccaa gtgccagaca      900
cctcagggcg ccatcaatag cagcctgccc ttccagaacg tgcacccgt gaccatcggc       960 gagtgcccca aatacgtgcg gagcaccaag ctgcggatgg tcaccggcct gagaaacatc     1020
cccagcatcc agagcagggg cctgttcgga gccattgccg gctttatcga gggcggctgg     1080
accggcatga tcgacgggtg gtacggctat caccaccaga acgagcaggg cagcggctac     1140
gccgccgatc agaagtctac ccagaacgcc atcaacggca tcaccaacaa agtgaacagc     1200
gtgatcgaga agatgaacac ccagttcacc gccgtgggca aagagttcaa caagctggaa     1260
cggcggatgg aaaacctgaa caagaaggtg gacgacggct tcctggacat ctggacctac     1320
aacgccgaac tgctggtgct gctggaaaac gagcggaccc tggacttcca cgacagcaac     1380
gtgaagaacc tgtacgagaa agtgaagtcc agctgaaga acaacgccaa agagatcggc     1440
aacggctgct tcgagttcta ccacaagtgc aacaacgagt gcatggaaag cgtgaagaat     1500
ggcacctacg actaccccaa gtacagcgag gaaagcaagc tgaaccgcga gaagatcgac     1560
ggcgtgaagc tggaatccat gggcgtgtac cagatcctgg ccatctatag caccgtggcc     1620
agcagcctgg tgctgctggt gtctctgggc gccatcagct tttggatgtg cagcaacggc     1680
agcctgcagt gccggatctg tatcggcagc atcggatcc                            1719
```

The invention claimed is:

1. An influenza virus-like particle (VLP) comprising an influenza hemagglutinin (HA) polypeptide, wherein the amino acid sequence of the HA polypeptide comprises:
   (i) no more than 5 amino acid substitutions relative to SEQ ID NO: 1;
   (ii) SEQ ID NO: 2;
   (iii) no more than 6 amino acid substitutions relative to SEQ ID NO: 3;
   (iv) no more than 8 amino acid substitutions relative to SEQ ID NO: 4;
   (v) no more than 10 amino acid substitutions relative to SEQ ID NO: 5;
   (vi) no more than 8 amino acid substitutions relative to SEQ ID NO: 6;
   (vii) no more than 10 amino acid substitutions relative to SEQ ID NO: 7;
   (viii) no more than 10 amino acid substitutions relative to SEQ ID NO: 8;
   (ix) SEQ ID NO: 9;
   (x) no more than 8 amino acid substitutions relative to SEQ ID NO: 10; or
   (xi) no more than 5 amino acid substitutions relative to SEQ ID NO: 11.

2. The influenza VLP of claim 1, wherein the influenza HA polypeptide comprises the amino acid sequence of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 10 or SEQ ID NO: 11.

3. The influenza VLP of claim 1, further comprising an influenza neuraminidase (NA) protein, an influenza matrix (M1) protein, or both.

4. A composition comprising the VLP of claim 1, and a pharmaceutically acceptable carrier.

5. A method of eliciting an immune response to influenza virus in a subject, comprising administering the VLP of claim 1 to the subject.

6. A method of immunizing a subject against influenza virus, comprising administering the VLP of claim 1 to the subject.

7. A method of eliciting an immune response to influenza virus in a subject, comprising administering the composition of claim 4 to the subject.

8. A method of immunizing a subject against influenza virus, comprising administering the composition of claim 4 to the subject.

9. The method of claim 8, wherein the composition further comprises an adjuvant.

10. The method of claim 8, wherein the composition is administered intramuscularly.

11. The method of claim 8, wherein the composition comprises about 1 to about 25 µg of the VLP.

12. The method of claim 8, wherein the composition comprises about 15 µg of the VLP.

13. A fusion protein comprising an influenza hemagglutinin (HA) polypeptide and a heterologous protein, wherein the amino acid sequence of the HA polypeptide comprises:
   (i) no more than 5 amino acid substitutions relative to SEQ ID NO: 1;
   (ii) SEQ ID NO: 2;
   (iii) no more than 6 amino acid substitutions relative to SEQ ID NO: 3;
   (iv) no more than 8 amino acid substitutions relative to SEQ ID NO: 4;
   (v) no more than 10 amino acid substitutions relative to SEQ ID NO: 5;
   (vi) no more than 8 amino acid substitutions relative to SEQ ID NO: 6;
   (vii) no more than 10 amino acid substitutions relative to SEQ ID NO: 7;
   (viii) no more than 10 amino acid substitutions relative to SEQ ID NO: 8;
   (ix) SEQ ID NO: 9;
   (x) no more than 8 amino acid substitutions relative to SEQ ID NO: 10; or
   (xi) no more than 5 amino acid substitutions relative to SEQ ID NO: 11.

14. A composition comprising the fusion protein of claim 13, and a pharmaceutically acceptable carrier.

15. A method of eliciting an immune response to influenza virus in a subject, comprising administering the fusion protein of claim 13 to the subject.

16. A method of eliciting an immune response to influenza virus in a subject, comprising administering the composition of claim 14 to the subject.

17. The method of claim 16, wherein the composition further comprises an adjuvant.

18. The method of claim 16, wherein the composition is administered intramuscularly.

* * * * *